(12) United States Patent
Christianson et al.

(10) Patent No.: US 10,758,346 B1
(45) Date of Patent: Sep. 1, 2020

(54) A2 CLIP FOR SIDE-DELIVERED TRANSCATHETER MITRAL VALVE PROSTHESIS

(71) Applicant: VDYNE, LLC, Maple Grove, MN (US)

(72) Inventors: Mark Christianson, Plymouth, MN (US); Robert Vidlund, Forest Lake, MN (US); Scott Kramer, Maple Grove, MN (US)

(73) Assignee: VDYNE, INC., Maple Grove, MN (US)

( * ) Notice: Subject to any disclaimer, the term of this patent is extended or adjusted under 35 U.S.C. 154(b) by 5 days.

(21) Appl. No.: 16/442,504

(22) Filed: Jun. 16, 2019

Related U.S. Application Data

(60) Provisional application No. 62/818,109, filed on Mar. 14, 2019.

(51) Int. Cl.
*A61F 2/24* (2006.01)

(52) U.S. Cl.
CPC .......... *A61F 2/2418* (2013.01); *A61F 2/2439* (2013.01); *A61F 2210/0014* (2013.01); *A61F 2220/0008* (2013.01); *A61F 2220/0033* (2013.01); *A61F 2230/0069* (2013.01); *A61F 2250/0098* (2013.01)

(58) Field of Classification Search
CPC .. A61F 2/24–2496; A61F 2/2427–2439; A61F 2/95–97; A61F 2002/2484–249; A61F 2002/9505–9665
See application file for complete search history.

(56) References Cited

U.S. PATENT DOCUMENTS

| | | |
|---|---|---|
| 5,397,351 A | 3/1995 | Pavcnik |
| 6,197,013 B1 | 3/2001 | Reed |
| 6,582,467 B1 | 6/2003 | Teitelbaum |
| 7,074,189 B1 | 7/2006 | Montegrande |
| 7,125,418 B2 | 10/2006 | Duran |
| 7,331,991 B2 | 2/2008 | Kheradvar |
| 7,374,571 B2 | 5/2008 | Pease |
| 7,449,027 B2 | 11/2008 | Hunt |
| 7,717,952 B2 | 5/2010 | Case |
| 7,753,949 B2 | 7/2010 | Lamphere |
| 7,828,840 B2 | 11/2010 | Biggs |
| 7,846,199 B2 | 12/2010 | Paul |
| 8,303,648 B2 | 11/2012 | Grewe |
| 8,366,768 B2 | 2/2013 | Zhang |
| 8,491,650 B2 | 7/2013 | Wiemeyer |
| 8,568,474 B2 | 10/2013 | Yeung |
| 8,641,752 B1 | 2/2014 | Holm |
| 8,696,743 B2 | 4/2014 | Holecek |
| 8,728,153 B2 | 5/2014 | Bishop |
| 8,758,395 B2 | 6/2014 | Kleshinski |
| 8,846,390 B2 | 9/2014 | Dove |
| 8,876,892 B2 | 11/2014 | Tran |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |

(Continued)

*Primary Examiner* — Katrina M Stransky
(74) *Attorney, Agent, or Firm* — Juneau & Mitchell; Todd L. Juneau

(57) ABSTRACT

The invention relates to an A2 clip for a side-delivered prosthetic mitral valve where the A2 clip is extended using a guide wire to capture native mitral leaflet and/or chordae tissue and withdrawing the guide wire contracts the A2 clip and pins the native tissue against the subannular sidewall of the prosthetic valve.

18 Claims, 16 Drawing Sheets

(56) References Cited

U.S. PATENT DOCUMENTS

| | | |
|---|---|---|
| 8,940,044 B2 | 1/2015 | Hammer |
| 8,956,404 B2 | 2/2015 | Börtlein |
| 9,011,524 B2 | 4/2015 | Eberhardt |
| 9,017,399 B2 | 4/2015 | Gross |
| 9,050,188 B2 | 4/2015 | Schweich |
| 9,072,604 B1 | 7/2015 | Melnick |
| 9,119,714 B2 | 9/2015 | Shandas |
| 9,216,076 B2 | 12/2015 | Mitra |
| 9,241,792 B2 | 1/2016 | Benichou |
| 9,248,016 B2 | 2/2016 | Oba |
| 9,259,215 B2 | 2/2016 | Chou |
| 9,277,990 B2 | 3/2016 | Klima |
| 9,289,282 B2 | 3/2016 | Olson |
| 9,289,296 B2 | 3/2016 | Braido |
| 9,295,547 B2 | 3/2016 | Costello |
| 9,301,839 B2 | 4/2016 | Stante |
| 9,456,899 B2 | 4/2016 | Yeung |
| 9,339,367 B2 | 5/2016 | Carpenter |
| 9,370,418 B2 | 6/2016 | Pintor |
| 9,381,083 B2 | 7/2016 | Costello |
| 9,387,075 B2 | 7/2016 | Börtlein |
| 9,393,111 B2 | 7/2016 | Ma |
| 9,433,500 B2 | 9/2016 | Chau |
| 9,440,054 B2 | 9/2016 | Bishop |
| 9,474,604 B2 | 10/2016 | Centola |
| 9,486,306 B2 | 11/2016 | Tegels |
| 9,510,941 B2 | 12/2016 | Bishop |
| 9,554,902 B2 | 1/2017 | Braido |
| 9,579,196 B2 | 2/2017 | Morriss |
| 9,579,200 B2 | 2/2017 | Lederman |
| 9,610,159 B2 | 4/2017 | Christianson |
| 9,615,925 B2 | 4/2017 | Subramanian |
| 9,629,719 B2 | 4/2017 | Rothstein |
| 9,636,222 B2 | 5/2017 | Oslund |
| 9,649,191 B2 | 5/2017 | Savage |
| 9,662,203 B2 | 5/2017 | Sheehan |
| 9,662,209 B2 | 5/2017 | Gross |
| 9,675,454 B2 | 6/2017 | Vidlund |
| 9,675,485 B2 | 6/2017 | Essinger |
| 9,687,343 B2 | 6/2017 | Börtlein |
| 9,707,076 B2 | 7/2017 | Stack |
| 9,713,530 B2 | 7/2017 | Cabiri |
| 9,750,607 B2 | 9/2017 | Ganesan |
| 9,763,778 B2 | 9/2017 | Börtlein |
| 9,763,779 B2 | 9/2017 | Börtlein |
| 9,839,511 B2 | 12/2017 | Ma |
| 9,849,011 B2 | 12/2017 | Zimmerman |
| 9,855,384 B2 | 1/2018 | Cohen |
| 9,861,464 B2 | 1/2018 | Azimpour |
| 10,058,426 B2 | 1/2018 | Barbarino |
| 9,895,219 B2 | 2/2018 | Costello |
| 9,901,330 B2 | 2/2018 | Akpinar |
| 9,918,838 B2 | 3/2018 | Ring |
| 9,943,409 B2 | 4/2018 | Kim |
| 9,949,825 B2 | 4/2018 | Braido |
| 9,968,444 B2 | 5/2018 | Millwee |
| 9,968,445 B2 | 5/2018 | Morriss |
| 9,980,815 B2 | 5/2018 | Nitzan |
| 9,987,121 B2 | 6/2018 | Blanzy |
| 10,010,411 B2 | 7/2018 | Peter |
| 10,010,412 B2 | 7/2018 | Taft |
| 10,022,054 B2 | 7/2018 | Najafi |
| 10,022,222 B2 | 7/2018 | Groothuis |
| 10,022,223 B2 | 7/2018 | Bruchman |
| 10,028,821 B2 | 7/2018 | Centola |
| 10,028,831 B2 | 7/2018 | Morin |
| 10,034,667 B2 | 7/2018 | Morris |
| 10,034,747 B2 | 7/2018 | Harewood |
| 10,039,638 B2 | 8/2018 | Bruchman |
| 10,058,315 B2 | 8/2018 | Rafiee |
| 10,058,411 B2 | 8/2018 | Fifer |
| 10,058,421 B2 | 8/2018 | Arai |
| 10,064,405 B2 | 9/2018 | Dale |
| 10,080,653 B2 | 9/2018 | Conklin |
| 10,085,835 B2 | 10/2018 | Thambar |
| 10,105,224 B2 | 10/2018 | Buchbinder |
| 10,117,741 B2 | 11/2018 | Schweich |
| 10,123,874 B2 | 11/2018 | Khairkhahan |
| 10,130,331 B2 | 11/2018 | Stigall |
| 10,130,467 B2 | 11/2018 | Braido |
| 10,149,685 B2 | 12/2018 | Kizuka |
| 10,154,905 B2 | 12/2018 | Duffy |
| 10,179,043 B2 | 1/2019 | Cohen-Tzemach |
| 10,182,908 B2 | 1/2019 | Tubishevitz |
| 10,182,911 B2 | 1/2019 | Hilukka |
| 10,206,775 B2 | 2/2019 | Kovalsky |
| 10,219,895 B2 | 3/2019 | Wagner |
| 10,219,896 B2 | 3/2019 | Sandstrom |
| 10,220,192 B2 | 3/2019 | Drasler |
| 10,226,178 B2 | 3/2019 | Cohen |
| 10,226,335 B2 | 3/2019 | Cartledge |
| 10,245,142 B2 | 4/2019 | Bonhoeffer |
| 10,258,467 B2 | 4/2019 | Hou |
| 10,265,173 B2 | 4/2019 | Griffin |
| 10,321,987 B2 | 6/2019 | Wang |
| 10,321,995 B1 | 6/2019 | Christianson |
| 10,327,895 B2 | 6/2019 | Lozonschi |
| 10,327,899 B2 | 6/2019 | Sandstrom |
| 10,329,066 B2 | 6/2019 | Kruetzfeldt |
| 10,350,047 B2 | 7/2019 | Rajpara |
| 10,357,361 B2 | 7/2019 | Rafi |
| 10,368,989 B2 | 8/2019 | Duffy |
| 10,398,550 B2 | 9/2019 | Chalekian |
| 10,426,611 B2 | 10/2019 | Hariton |
| 10,433,957 B2 | 10/2019 | Khouengboua |
| 10,433,960 B1 | 10/2019 | Sutherland |
| 2003/0040772 A1 | 2/2003 | Hyodoh et al. |
| 2003/0153901 A1 | 8/2003 | Herweck |
| 2003/0166990 A1 | 9/2003 | Trauthen |
| 2003/0171801 A1 | 9/2003 | Bates |
| 2006/0015167 A1 | 1/2006 | Armstrong |
| 2006/0195180 A1 | 8/2006 | Kheradvar |
| 2006/0271098 A1 | 11/2006 | Peacock |
| 2007/0027535 A1 | 2/2007 | Purdy |
| 2007/0032850 A1 | 2/2007 | Ruiz |
| 2007/0038295 A1 | 2/2007 | Case |
| 2007/0162102 A1 | 7/2007 | Ryan |
| 2007/0208417 A1 | 9/2007 | Agnew |
| 2007/0213805 A1 | 9/2007 | Schaeffer |
| 2007/0233176 A1 | 10/2007 | Gilsen |
| 2007/0233228 A1 | 10/2007 | Eberhardt |
| 2007/0288087 A1 | 12/2007 | Fearnot |
| 2008/0004686 A1 | 1/2008 | Hunt |
| 2008/0020013 A1 | 1/2008 | Reyes |
| 2008/0132999 A1 | 6/2008 | Mericle |
| 2008/0200977 A1 | 8/2008 | Paul |
| 2008/0208332 A1 | 8/2008 | Lamphere |
| 2008/0262609 A1 | 10/2008 | Gross |
| 2008/0275550 A1 | 11/2008 | Kheradvar |
| 2009/0094189 A1 | 4/2009 | Stephens |
| 2009/0192586 A1 | 7/2009 | Tabor |
| 2009/0254174 A1 | 10/2009 | Case |
| 2009/0264991 A1 | 10/2009 | Paul |
| 2009/0287290 A1 | 11/2009 | Macaulay |
| 2010/0160773 A1 | 6/2010 | Cohen |
| 2010/0161043 A1 | 6/2010 | Maisano |
| 2010/0168844 A1 | 7/2010 | Toomes |
| 2010/0174363 A1 | 7/2010 | Castro |
| 2010/0179583 A1 | 7/2010 | Carpenter |
| 2010/0179584 A1 | 7/2010 | Carpenter |
| 2010/0179647 A1 | 7/2010 | Carpenter |
| 2010/0305685 A1 | 12/2010 | Millwee |
| 2011/0029071 A1 | 2/2011 | Zlotnick |
| 2011/0098804 A1 | 4/2011 | Yeung |
| 2011/0125145 A1 | 5/2011 | Mody |
| 2011/0172764 A1 | 7/2011 | Badhwar |
| 2011/0245917 A1 | 10/2011 | Savage |
| 2011/0251675 A1 | 10/2011 | Dwork |
| 2011/0257721 A1 | 10/2011 | Tabor |
| 2012/0022633 A1 | 1/2012 | Olson |
| 2012/0022640 A1 | 1/2012 | Gross |
| 2012/0022644 A1 | 1/2012 | Reich |
| 2012/0035701 A1 | 2/2012 | To |
| 2012/0123531 A1 | 5/2012 | Tsukashima |

(56) References Cited

U.S. PATENT DOCUMENTS

| | | |
|---|---|---|
| 2012/0137521 A1 | 6/2012 | Millwee |
| 2012/0172981 A1 | 7/2012 | DuMontelle |
| 2012/0209375 A1 | 8/2012 | Madrid |
| 2012/0232574 A1 | 9/2012 | Kim |
| 2012/0277853 A1 | 11/2012 | Rothstein |
| 2013/0055941 A1 | 3/2013 | Holecek |
| 2013/0131714 A1 | 5/2013 | Wang |
| 2013/0131792 A1 | 5/2013 | Miller |
| 2013/0166017 A1 | 6/2013 | Cartledge |
| 2013/0184742 A1 | 7/2013 | Ganesan |
| 2013/0190857 A1 | 7/2013 | Mitra |
| 2013/0197621 A1 | 8/2013 | Ryan |
| 2013/0226289 A1 | 8/2013 | Shaolian |
| 2013/0238010 A1 | 9/2013 | Johnson |
| 2013/0253570 A1 | 9/2013 | Bates |
| 2013/0274618 A1 | 10/2013 | Hou |
| 2013/0274855 A1 | 10/2013 | Stante |
| 2013/0282110 A1 | 10/2013 | Schweich |
| 2013/0297010 A1 | 11/2013 | Bishop |
| 2013/0331929 A1 | 12/2013 | Mitra |
| 2014/0000112 A1 | 1/2014 | Braido |
| 2014/0005540 A1 | 1/2014 | Merhi |
| 2014/0005768 A1 | 1/2014 | Thomas |
| 2014/0039511 A1 | 2/2014 | Morris |
| 2014/0081383 A1 | 3/2014 | Eberhardt |
| 2014/0088680 A1 | 3/2014 | Costello |
| 2014/0107758 A1 | 4/2014 | Glazier |
| 2014/0110279 A1 | 4/2014 | Kruetzfeldt |
| 2014/0114403 A1 | 4/2014 | Dale |
| 2014/0135895 A1 | 5/2014 | Andress |
| 2014/0172070 A1 | 6/2014 | Seguin |
| 2014/0180069 A1 | 6/2014 | Millett |
| 2014/0180070 A1 | 6/2014 | Millett |
| 2014/0194704 A1 | 7/2014 | Millett |
| 2014/0214069 A1 | 7/2014 | Franklin |
| 2014/0214159 A1 | 7/2014 | Vidlund |
| 2014/0222137 A1 | 8/2014 | Miller |
| 2014/0249566 A1 | 9/2014 | Quinn |
| 2014/0276616 A1 | 9/2014 | Smith |
| 2014/0276971 A1 | 9/2014 | Kovach |
| 2014/0277388 A1 | 9/2014 | Skemp |
| 2014/0277408 A1 | 9/2014 | Folan |
| 2014/0296969 A1 | 10/2014 | Tegels |
| 2014/0303718 A1 | 10/2014 | Tegels |
| 2014/0303724 A1 | 10/2014 | Bluestein |
| 2014/0309732 A1 | 10/2014 | Solem |
| 2014/0324161 A1 | 10/2014 | Tegels |
| 2014/0350662 A1 | 11/2014 | Vaturi |
| 2014/0371789 A1 | 12/2014 | Harton |
| 2014/0379076 A1 | 12/2014 | Vidlund |
| 2015/0005808 A1 | 1/2015 | Chouinard |
| 2015/0005874 A1 | 1/2015 | Vidlund |
| 2015/0039081 A1 | 2/2015 | Costello |
| 2015/0051687 A1 | 2/2015 | Dickerhoff |
| 2015/0094802 A1 | 4/2015 | Buchbinder |
| 2015/0112188 A1 | 4/2015 | Stigall |
| 2015/0119982 A1 | 4/2015 | Quill |
| 2015/0127093 A1 | 5/2015 | Hosmer |
| 2015/0142103 A1 | 5/2015 | Vidlund |
| 2015/0196391 A1 | 7/2015 | Dwork |
| 2015/0202044 A1 | 7/2015 | Chau |
| 2015/0216661 A1 | 8/2015 | Hacohen |
| 2015/0230919 A1 | 8/2015 | Chau |
| 2015/0245934 A1 | 9/2015 | Lombardi |
| 2015/0257880 A1 | 9/2015 | Börtlein |
| 2015/0257882 A1 | 9/2015 | Börtlein |
| 2015/0272731 A1 | 10/2015 | Racchini |
| 2015/0289971 A1 | 10/2015 | Costello |
| 2015/0289975 A1 | 10/2015 | Costello |
| 2015/0297241 A1 | 10/2015 | Yodfat |
| 2015/0305867 A1 | 10/2015 | Liu |
| 2015/0313701 A1 | 11/2015 | Krahbichler |
| 2015/0324717 A1 | 12/2015 | O'Donnell |
| 2015/0351904 A1 | 12/2015 | Cooper |
| 2015/0359629 A1 | 12/2015 | Ganesan |
| 2016/0008130 A1 | 1/2016 | Hasin |
| 2016/0008131 A1* | 1/2016 | Christianson ......... A61B 17/10 623/2.11 |
| 2016/0022417 A1 | 1/2016 | Karapetian |
| 2016/0030165 A1 | 2/2016 | Mitra |
| 2016/0030167 A1 | 2/2016 | Delaloye |
| 2016/0038283 A1 | 2/2016 | Divekar |
| 2016/0045165 A1 | 2/2016 | Braido |
| 2016/0045306 A1 | 2/2016 | Agrawal |
| 2016/0045309 A1 | 2/2016 | Valdez |
| 2016/0067031 A1 | 3/2016 | Kassab |
| 2016/0081799 A1 | 3/2016 | Leo |
| 2016/0095703 A1 | 4/2016 | Thomas |
| 2016/0095704 A1 | 4/2016 | Whitman |
| 2016/0113764 A1 | 4/2016 | Sheahan |
| 2016/0113766 A1 | 4/2016 | Ganesan |
| 2016/0113768 A1 | 4/2016 | Ganesan |
| 2016/0143721 A1 | 5/2016 | Rosenbluth |
| 2016/0143730 A1 | 5/2016 | Kheradvar |
| 2016/0143735 A1 | 5/2016 | Subramanian |
| 2016/0143739 A1 | 5/2016 | Horgan |
| 2016/0158004 A1 | 6/2016 | Kumar |
| 2016/0158007 A1 | 6/2016 | Centola |
| 2016/0158008 A1 | 6/2016 | Miller |
| 2016/0166382 A1 | 6/2016 | Nguyen |
| 2016/0184488 A1 | 6/2016 | Toyoda |
| 2016/0194425 A1 | 7/2016 | Mitra |
| 2016/0213470 A1 | 7/2016 | Ahlberg |
| 2016/0220367 A1 | 8/2016 | Barrett |
| 2016/0220372 A1 | 8/2016 | Medema |
| 2016/0220734 A1 | 8/2016 | Dyamenahalli |
| 2016/0228250 A1 | 8/2016 | Casley |
| 2016/0235530 A1 | 8/2016 | Thomas |
| 2016/0256269 A1 | 9/2016 | Cahalane |
| 2016/0256270 A1 | 9/2016 | Folan |
| 2016/0270911 A1 | 9/2016 | Ganesan |
| 2016/0303804 A1 | 10/2016 | Grbic |
| 2016/0310274 A1 | 10/2016 | Gross |
| 2016/0317301 A1 | 11/2016 | Quadri |
| 2016/0324639 A1 | 11/2016 | Nguyen |
| 2016/0331534 A1 | 11/2016 | Buchbinder |
| 2016/0354201 A1 | 12/2016 | Keough |
| 2016/0361169 A1 | 12/2016 | Gross |
| 2016/0361184 A1 | 12/2016 | Tabor |
| 2016/0367364 A1 | 12/2016 | Torrianni |
| 2017/0000603 A1 | 1/2017 | Conklin |
| 2017/0000604 A1 | 1/2017 | Conklin |
| 2017/0035562 A1 | 2/2017 | Quadri |
| 2017/0056171 A1 | 3/2017 | Cooper |
| 2017/0071736 A1 | 3/2017 | Zhu |
| 2017/0076014 A1 | 3/2017 | Bressloff |
| 2017/0079786 A1 | 3/2017 | Li |
| 2017/0079795 A1 | 3/2017 | Morrissey |
| 2017/0100246 A1 | 4/2017 | Rust |
| 2017/0112620 A1 | 4/2017 | Curley |
| 2017/0128208 A1 | 5/2017 | Christianson |
| 2017/0143488 A1 | 5/2017 | Lashinski |
| 2017/0143489 A1 | 5/2017 | Lashinski |
| 2017/0165065 A1 | 6/2017 | Rothstein |
| 2017/0181851 A1 | 6/2017 | Annest |
| 2017/0189177 A1 | 7/2017 | Schweich |
| 2017/0196690 A1 | 7/2017 | Racchini |
| 2017/0209266 A1 | 7/2017 | Lane |
| 2017/0216030 A1 | 8/2017 | Joensson |
| 2017/0224480 A1 | 8/2017 | Garde |
| 2017/0224486 A1 | 8/2017 | Delaloye |
| 2017/0231755 A1 | 8/2017 | Gloss |
| 2017/0231760 A1 | 8/2017 | Lane |
| 2017/0239047 A1 | 8/2017 | Quill |
| 2017/0245994 A1 | 8/2017 | Khairkhahan |
| 2017/0252163 A1 | 9/2017 | Kheradvar |
| 2017/0258584 A1 | 9/2017 | Chang |
| 2017/0258585 A1 | 9/2017 | Marquez |
| 2017/0273784 A1 | 9/2017 | Racchini |
| 2017/0281337 A1 | 10/2017 | Campbell |
| 2017/0296340 A1 | 10/2017 | Gross |
| 2017/0325976 A1 | 11/2017 | Nguyen |
| 2017/0333184 A1 | 11/2017 | Ryan |
| 2017/0348099 A1 | 12/2017 | Mendelson |

(56) References Cited

U.S. PATENT DOCUMENTS

| | | |
|---|---|---|
| 2017/0348100 A1 | 12/2017 | Lane |
| 2017/0360558 A1 | 12/2017 | Ma |
| 2017/0360561 A1 | 12/2017 | Bell |
| 2018/0035971 A1 | 2/2018 | Brenner |
| 2018/0042549 A1 | 2/2018 | Ho |
| 2018/0042723 A1 | 2/2018 | Yellin |
| 2018/0043133 A1 | 2/2018 | Wong |
| 2018/0049875 A1 | 2/2018 | Iflah |
| 2018/0049876 A1 | 2/2018 | Mikraki |
| 2018/0055628 A1 | 3/2018 | Patel |
| 2018/0055633 A1 | 3/2018 | Costello |
| 2018/0056045 A1 | 3/2018 | Donoghue |
| 2018/0056046 A1 | 3/2018 | Kiersey |
| 2018/0071088 A1 | 3/2018 | Badhwar |
| 2018/0078367 A1 | 3/2018 | Saar |
| 2018/0078368 A1 | 3/2018 | Vidlund |
| 2018/0078370 A1 | 3/2018 | Kovalsky |
| 2018/0085219 A1 | 3/2018 | Krivoruchko |
| 2018/0098837 A1 | 4/2018 | Shahriari |
| 2018/0099124 A1 | 4/2018 | McLoughlin |
| 2018/0116843 A1 | 5/2018 | Schreck |
| 2018/0125642 A1 | 5/2018 | White |
| 2018/0125654 A1 | 5/2018 | Duffy |
| 2018/0126127 A1 | 5/2018 | Devereux |
| 2018/0133000 A1 | 5/2018 | Scheinblum |
| 2018/0133006 A1 | 5/2018 | Jones |
| 2018/0133011 A1 | 5/2018 | Perouse |
| 2018/0140417 A1 | 5/2018 | Sciscio |
| 2018/0147041 A1 | 5/2018 | Choinard |
| 2018/0161158 A1 | 6/2018 | Kovalsky |
| 2018/0161161 A1 | 6/2018 | Yellin |
| 2018/0168793 A1 | 6/2018 | Lees |
| 2018/0177580 A9 | 6/2018 | Shemesh |
| 2018/0177594 A1 | 6/2018 | Patel |
| 2018/0185153 A1 | 7/2018 | Bishop |
| 2018/0193138 A1 | 7/2018 | Vidlund |
| 2018/0200049 A1* | 7/2018 | Chambers ............ A61F 2/2436 |
| 2018/0214141 A1 | 8/2018 | Mendez |
| 2018/0221016 A1 | 8/2018 | Conklin |
| 2018/0243071 A1 | 8/2018 | Eigler |
| 2018/0243532 A1 | 8/2018 | Willard |
| 2018/0256322 A1 | 9/2018 | Zhang |
| 2018/0256327 A1 | 9/2018 | Perszyk |
| 2018/0280174 A1 | 10/2018 | Dwork |
| 2018/0289474 A1 | 10/2018 | Rajagopal |
| 2018/0289475 A1 | 10/2018 | Chung |
| 2018/0289485 A1 | 10/2018 | Rajagopal |
| 2018/0296335 A1 | 10/2018 | Miyashiro |
| 2018/0296337 A1 | 10/2018 | Duhay |
| 2018/0303488 A1 | 10/2018 | Hill |
| 2018/0311474 A1 | 11/2018 | Tyler |
| 2018/0318073 A1 | 11/2018 | Tseng |
| 2018/0318078 A1 | 11/2018 | Willard |
| 2018/0325665 A1 | 11/2018 | Gurovich |
| 2018/0325671 A1 | 11/2018 | Abunassar |
| 2018/0338832 A1 | 11/2018 | Ganesan |
| 2018/0353293 A1 | 12/2018 | Colavito |
| 2018/0353295 A1 | 12/2018 | Cooper |
| 2018/0360439 A1 | 12/2018 | Niland |
| 2018/0360599 A1 | 12/2018 | Drasler |
| 2019/0008640 A1 | 1/2019 | Cooper |
| 2019/0015188 A1 | 1/2019 | Eigler |
| 2019/0021834 A1 | 1/2019 | Nir |
| 2019/0029823 A1 | 1/2019 | Nguyen |
| 2019/0038404 A1 | 2/2019 | Iamberger |
| 2019/0038405 A1 | 2/2019 | Iamberger |
| 2019/0053894 A1 | 2/2019 | Levi |
| 2019/0053897 A1 | 2/2019 | Levi |
| 2019/0053898 A1 | 2/2019 | Maimon |
| 2019/0053899 A1 | 2/2019 | Levi |
| 2019/0060051 A1 | 2/2019 | Scheeff |
| 2019/0060059 A1 | 2/2019 | Delgado |
| 2019/0060069 A1 | 2/2019 | Maimon |
| 2019/0060071 A1 | 2/2019 | Lane |
| 2019/0091022 A1 | 2/2019 | Levi |
| 2019/0070003 A1 | 3/2019 | Siegel |
| 2019/0076233 A1 | 3/2019 | Fish |
| 2019/0076249 A1 | 3/2019 | Khairkhahan |
| 2019/0083085 A1 | 3/2019 | Gilmore |
| 2019/0091005 A1 | 3/2019 | Fifer |
| 2019/0091015 A1 | 3/2019 | Dienno |
| 2019/0091018 A1 | 3/2019 | Hariton |
| 2019/0099265 A1 | 4/2019 | Braido |
| 2019/0099270 A1 | 4/2019 | Morrissey |
| 2019/0105153 A1 | 4/2019 | Barash |
| 2019/0117223 A1 | 4/2019 | Abunassar |
| 2019/0117387 A1 | 4/2019 | Li |
| 2019/0117391 A1 | 4/2019 | Humair |
| 2019/0117400 A1 | 4/2019 | Medema |
| 2019/0117401 A1 | 4/2019 | Cortez |
| 2019/0125287 A1 | 5/2019 | Itou |
| 2019/0125536 A1 | 5/2019 | Prabhu |
| 2019/0133528 A1 | 5/2019 | Kassab |
| 2019/0133756 A1 | 5/2019 | Zhang |
| 2019/0133757 A1 | 5/2019 | Zhang |
| 2019/0133765 A1 | 5/2019 | Yellin |
| 2019/0142566 A1 | 5/2019 | Lansky |
| 2019/0142582 A1 | 5/2019 | Drasler |
| 2019/0150867 A1 | 5/2019 | Itou |
| 2019/0151509 A1 | 5/2019 | Kheradvar |
| 2019/0167423 A1 | 6/2019 | Hariton |
| 2019/0167429 A1 | 6/2019 | Stearns |
| 2019/0175338 A1 | 6/2019 | White |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp |
| 2019/0192287 A1 | 6/2019 | Sandstrom |
| 2019/0192296 A1 | 6/2019 | Schwartz |
| 2019/0209317 A1 | 7/2019 | Zhang |
| 2019/0209320 A1 | 7/2019 | Drasler |
| 2019/0231523 A1 | 8/2019 | Lombardi |
| 2019/0240020 A1 | 8/2019 | Rafiee |
| 2019/0240022 A1 | 8/2019 | Rafiee |
| 2019/0247050 A1 | 8/2019 | Goldsmith |
| 2019/0254815 A1 | 8/2019 | Bruchman |
| 2019/0254816 A1 | 8/2019 | Anderson |
| 2019/0262118 A1 | 8/2019 | Eigler |
| 2019/0262129 A1 | 8/2019 | Cooper |
| 2019/0269413 A1 | 9/2019 | Yodfat |
| 2019/0269504 A1 | 9/2019 | Wang |
| 2019/0269839 A1 | 9/2019 | Wilson |
| 2019/0282360 A1 | 9/2019 | Colavito |
| 2019/0290426 A1 | 9/2019 | Maimon |
| 2019/0290427 A1 | 9/2019 | Mantanus |
| 2019/0307563 A1 | 10/2019 | Sandstrom |
| 2019/0307589 A1 | 10/2019 | Goldberg |

\* cited by examiner

A2 CLIP FOR SIDE-DELIVERED TRANSCATHETER MITRAL VALVE PROSTHESIS

CROSS-REFERENCE TO RELATED APPLICATIONS

Provided by Application Data Sheet per USPTO rules.

STATEMENT REGARDING FEDERALLY SPONSORED R&D

Provided by Application Data Sheet per with USPTO rules.

NAMES OF PARTIES TO JOINT RESEARCH AGREEMENT

Provided by Application Data Sheet per with USPTO rules.

REFERENCE TO SEQUENCE LISTING

Provided by Application Data Sheet per USPTO rules.

STATEMENT RE PRIOR DISCLOSURES

Provided by Application Data Sheet per USPTO rules.

BACKGROUND OF THE INVENTION

Field of the Invention

The invention relates to an extendable A2 clip for a side-delivered transcatheter mitral valve replacement (A61F2/2412).

DESCRIPTION OF THE RELATED ART

In 1952 surgeons implanted the first mechanical heart valve, a ball valve that could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting dic technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The present invention is directed to an A2 clip for a side-delivered prosthetic mitral valve where the A2 clip extends with or without a guide wire to capture and pin native mitral leaflet and/or chordae tissue against the subannular sidewall of the prosthetic valve.

Use of an side-delivered transcatheter mitral valve replacement allows a very large diameter valve to be delivered and deployed from the inferior vena cava trans-septally into the mitral valve, e.g. has a height of about 5-60 mm and a diameter of about 25-80 mm, without requiring an oversized diameter catheter and without requiring delivery and deployment from a catheter at an acute angle of approach.

Side-delivered mitral valves have a collapsible outer frame and collapsible inner flow control component that are foldable along a horizontal axis (z-axis, axis parallel to central axis of delivery catheter) and compressible along a vertical axis (y-axis).

Accordingly, the present invention is directed to a side-delivered mitral valve having an A2 anterior leaflet anchoring tab component, comprising:
(i) a self-expanding annular outer support frame, said annular support frame having a central channel and an outer perimeter wall circumscribing a central vertical y-axis in an expanded configuration, said outer perimeter wall having an anterior side, a posterior side, a distal side and a proximal side,
(ii) an integrated subannular A2 anterior leaflet anchoring system mounted on the anterior side of the outer perimeter wall, wherein the system comprises
an A2 clip sleeve having a pre-loaded A2 clip disposed within a lumen of the sleeve, the pre-loaded A2 clip comprising an elongated loop or tab, wherein said A2 clip is compressed or folded within the sleeve and a distal portion of the A2 clip presses against the perimeter wall when said A2 clip is compressed or folded, and wherein said A2 clip is extended or unfolded when released from the sleeve along the cylindrical axis for capture of native leaflet or chordae tissue,
wherein the A2 clip is self-actuated by release of hold-down element or engages with a guide wire during deployment to an extended or unfolded position allowing the A2 clip to capture native leaflet and/or native chordae, and upon withdrawal of the guide wire, the native leaflet and/or native chordae are sandwiched between the A2 clip and the perimeter wall of the annular support frame;

(iii) a collapsible flow control component mounted within the annular support frame, the outer support frame and the leaflet frame comprising diamond- or eye-shaped wire cells made from heat-set Nitinol and configured to be foldable along a z-axis from a rounded or cylindrical configuration to a flattened cylinder configuration having a width of 8-12 mm, and compressible along a vertical axis y-axis to a shortened configuration having a height of 8-12 mm, the collapsible (inner) flow control component having a leaflet frame with 2-4 flexible leaflets mounted thereon, wherein the 2-4 leaflets are configured to permit blood flow in a first direction through an inflow end of the flow control component and block blood flow in a second direction, opposite the first direction, through an outflow end of the flow control component;

(iv) a distal anchoring tab mounted on the distal side of the annular support frame, wherein the tab is an elongated member attached at a first end to the perimeter wall of the annular support frame and has an unattached second end that is heat set to a folded position to press against the perimeter wall, wherein the tab engages with a guide wire during deployment to an opened configuration, wherein the tab in the opened configuration tracks over the guide wire allowing the tab to capture native leaflet and/or native chordae, and upon withdrawal of the guide wire releasing the tab to the folded position, the native leaflet and/or native chordae are sandwiched between the folded tab and the perimeter wall of the annular support frame; wherein the valve is compressible to a compressed configuration for introduction into the body using a delivery catheter for implanting at a desired location in the body, said compressed configuration is oriented along a horizontal x-axis at an intersecting angle of between 45-135 degrees to the central vertical y-axis, and expandable to an expanded configuration having a horizontal x-axis at an intersecting angle of between 45-135 degrees to the central vertical y-axis, wherein the horizontal x-axis of the compressed configuration of the valve is substantially parallel to a length-wise cylindrical axis of the delivery catheter, wherein the valve has a height of about 5-60 mm and a diameter of about 25-80 mm.

In another preferred embodiment, the invention provides a valve as described and claimed, wherein the A2 clip has a radio-opaque marker.

In another preferred embodiment, the invention provides a valve as described and claimed, wherein the A2 clip comprises braided polyethylene, treated pericardial tissue, ePTFE, or Nitinol.

In another preferred embodiment, the invention provides a valve as described and claimed, wherein the annular support frame is comprised of a plurality of compressible wire cells having a orientation and cell geometry substantially orthogonal to the central vertical axis to minimize wire cell strain when the annular support frame is configured in a vertical compressed configuration, a rolled compressed configuration, or a folded compressed configuration.

In another preferred embodiment, the invention provides a valve as described and claimed, wherein the annular support frame has a lower body portion and an upper collar portion, wherein the lower body portion in an expanded configuration forms a shape selected from a funnel, cylinder, flat cone, or circular hyperboloid.

In another preferred embodiment, the invention provides a valve as described and claimed, wherein said annular support frame is comprised of a braided, wire, or laser-cut wire frame, and said annular support frame is covered with a biocompatible material.

In another preferred embodiment, the invention provides a valve as described and claimed, wherein the annular support frame has a side profile of a flat cone shape having a diameter R of 40-80 mm, a diameter r of 20-60 mm, and a height of 5-60 mm.

In another preferred embodiment, the invention provides a valve as described and claimed, wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In another preferred embodiment, the invention provides a valve as described and claimed, wherein the annular support frame has a side profile of an hourglass shape having a top diameter R1 of 40-80 mm, a bottom diameter R2 of 50-70 mm, an internal diameter r of 20-60 mm, and a height of 5-60 mm. In another preferred embodiment, the invention provides a valve as described and claimed, wherein the valve in an expanded configuration has a central vertical y-axis that is substantially parallel to the first direction.

In another preferred embodiment, the invention provides a valve as described and claimed, wherein the flow control component has an internal diameter of 20-60 mm and a height of 10-40 mm, and a plurality of leaflets of pericardial material joined to form a rounded cylinder at an inflow end and having a flat closable aperture at an outflow end.

In another preferred embodiment, the invention provides a valve as described and claimed, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

In another preferred embodiment, the invention provides a valve as described and claimed, wherein the distal anchoring tab is comprised of wire loop, a wire frame, a laser cut frame, an integrated frame section, or a stent, and the distal anchoring tab extends from about 10-40 mm away from the distal side of the annular support frame.

In another preferred embodiment, the invention provides a valve as described and claimed, further comprising an upper distal anchoring tab attached to a distal upper edge of the annular support frame, the upper distal anchoring tab comprised of wire loop, a wire frame, a laser cut frame, an integrated frame section, or a stent, and extends from about 2-20 mm away from the annular support frame.

In another preferred embodiment, the invention provides a valve as described and claimed, comprising at least one tissue anchor connected to the annular support frame for engaging native tissue.

In another preferred embodiment, the invention provides a valve as described and claimed, wherein the outer perimeter wall comprises a front wall portion that is a first flat panel and a back wall portion that is a second flat panel, and wherein a proximal fold area and a distal fold area each comprise a sewn seam, a fabric panel, a rigid hinge, or a flexible fabric span without any wire cells.

In another preferred embodiment, the invention provides a valve as described and claimed, wherein the annular support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

In another preferred embodiment, the invention provides a method for side delivery of implantable prosthetic mitral valve to a patient, the method comprising the steps:

advancing a guide wire trans-septally to the left atrium, through the annular plane at the A1/P1 commissure, to a position behind a native P2 leaflet of a mitral valve of the patient;

advancing the valve of claim 1 in a delivery catheter to the left atrium of the patient, said valve in a compressed configuration for side-delivery, wherein the distal anchoring tab is threaded onto the guide wire, and wherein the A2 clip is optionally threaded onto the guide wire;

releasing the prosthetic mitral valve from the delivery catheter, wherein the tab is in an open configuration and tracks over the guide wire during release;

advancing the prosthetic mitral valve over the guide wire to move the tab to the position behind the native posterior leaflet and to seat the prosthetic mitral valve into the native annulus;

withdrawing the guide wire to a first distal tab release position to release the distal tab to the folded position allowing the tab to capture native leaflet and/or native chordae, and sandwich the native leaflet and/or chordae between the folded tab and the perimeter wall of the annular support frame; and optionally withdrawing the guide wire to a second A2 clip release position to release the A2 clip to the open position allowing the A2 clip to capture native leaflet and/or native chordae, and sandwich the native leaflet and/or native chordae between the A2 clip and the perimeter wall of the annular support frame.

In another preferred embodiment, the invention provides a method as described and claimed, wherein releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In another preferred embodiment, the invention provides a method as described and claimed, comprising the additional step of anchoring one or more tissue anchors attached to the valve into native tissue.

In another preferred embodiment, the invention provides a valve as described and claimed, comprising the additional step of rotating the heart valve prosthesis using a steerable catheter along an axis parallel to the plane of the valve annulus.

BRIEF DESCRIPTION OF THE SEVERAL VIEWS OF DRAWING

FIG. 1 is an illustration of a SIDE PERSPECTIVE view of a sidely deliverable transcatheter heart valve with an extendable self-contracting distal anchoring tab. FIG. 1 shows collapsible flow control component mounted within the annular outer support frame, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, according to the invention.

FIG. 6 (a)-(d) is an illustration of an A2 clip in a pocket or sleeve that would be mounted on the perimeter wall of the outer frame. FIG. 6(a) shows an A2 clip stowed in the pocket before deployment. FIG. 6(b) shows an A2 clip extended in an ventricular direction along the central axis. FIG. 6(c) shows an A2 clip completely unfolded for capturing anterior tissue. FIG. 6(d) shows a retracted, re-folded A2 clip in a position after capture of tissue where the tissue (not shown) is pinned against the perimeter wall of the outer frame.

FIG. 7(a)-(h) is an illustration of a variety of anchor loop configurations contemplated for use as a distal portion of the A2 clip.

Figure 8:
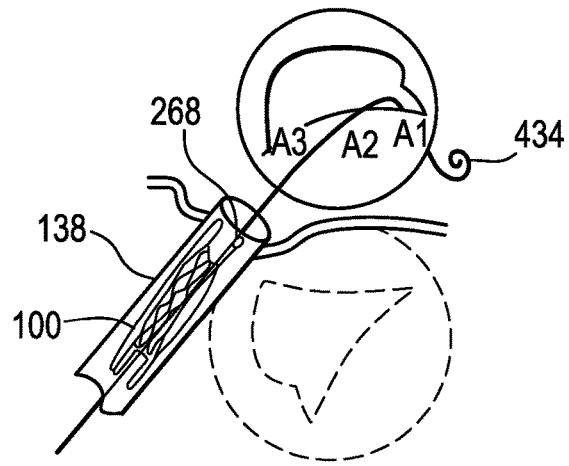

FIG. 8 is an illustration of a TOP view of a mitral valve and shows guide wire directing the replacement valve to the A1 leaflet with the valve in a compressed intra-catheter configuration, according to the invention.

Figure 9:
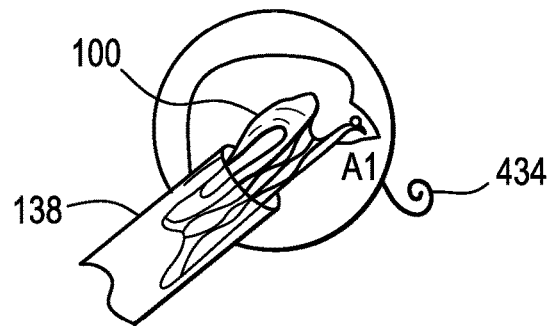

FIG. 9 is an illustration of a TOP view of a mitral valve and prosthetic valve with an overwire tab positioning the valve into the A1 area, and the valve in a partial deployment stage being partially expelled, according to the invention.

Figure 10:
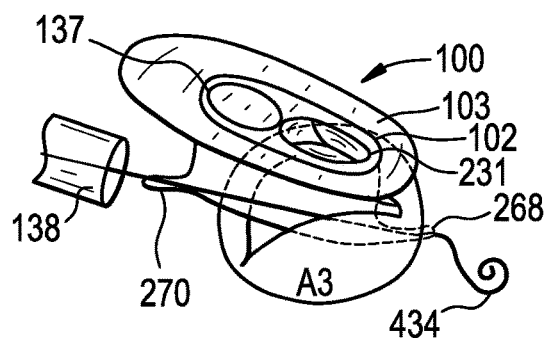

FIG. 10 is an illustration of a TOP PERSPECTIVE view of a prosthetic valve that is fully expelled and positioned temporarily at an upwards angle with a distal anchoring tab in the A1 area, and a proximal collar above the mitral valve allowing for the new prosthetic valve to engage the blood flow while the native mitral valve continues to operate, just prior to the proximal side being shoe-horned into place, for a non-traumatic transition from native valve to prosthetic valve, according to the invention.

Figure 11:
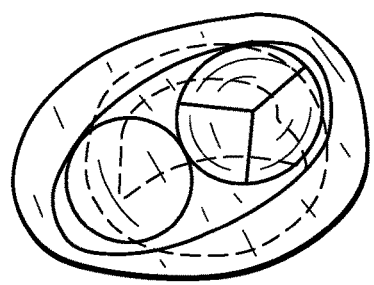

FIG. 11 is an illustration of a TOP view of a prosthetic valve deployed in the native annulus (not visible—in dashed line), according to the invention.

Figure 12:
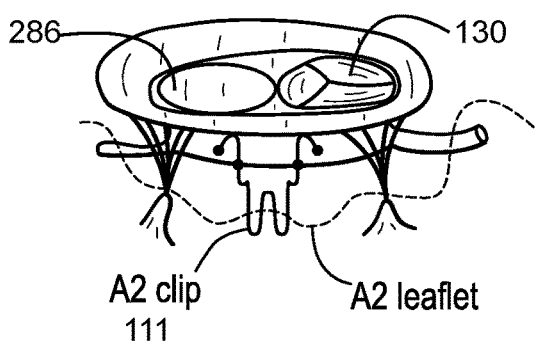

FIG. 12 is an illustration of a SIDE PERSPECTIVE view of a prosthetic valve deployed in the native annulus (not visible) with an A2 clip in the extended position, according to the invention.

Figure 13:
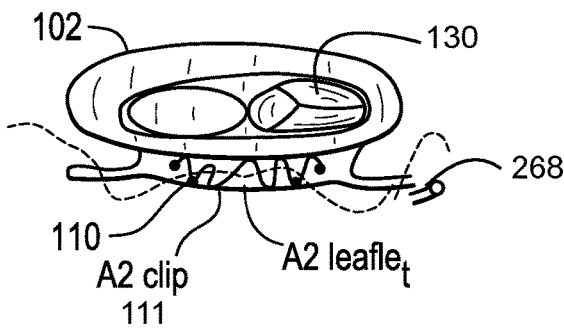

FIG. 13 is an illustration of a SIDE PERSPECTIVE view of an embodiment of a prosthetic valve having an A2 clip integrated into the sidewall of the A2 facing side of the outer frame of the valve with the A2 clip in the retracted position, according to the invention.

Figure 14A:
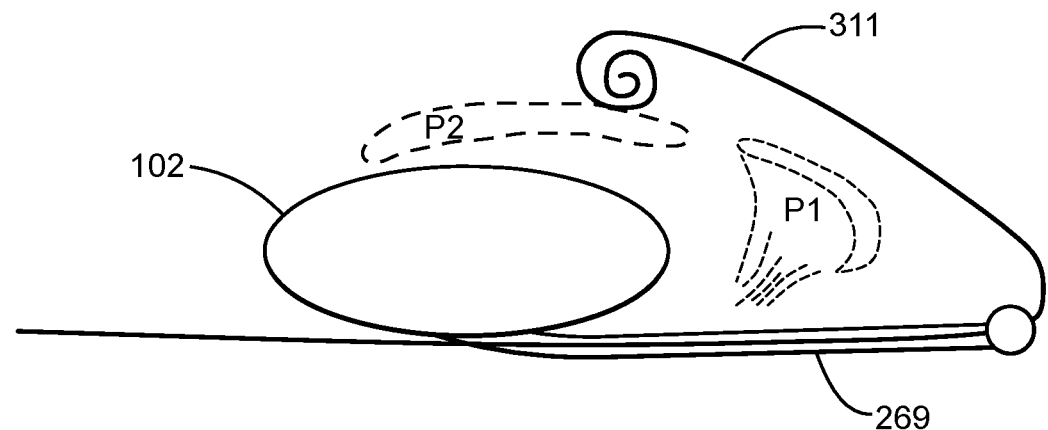
Figure 14B:
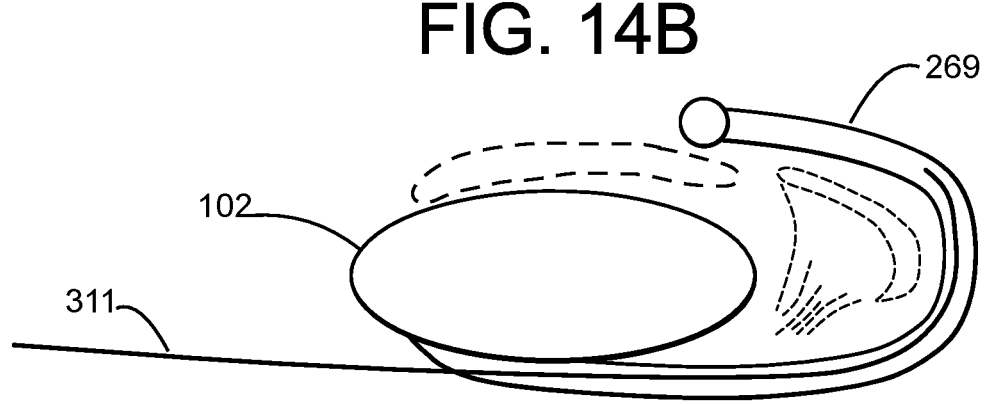
Figure 14C:
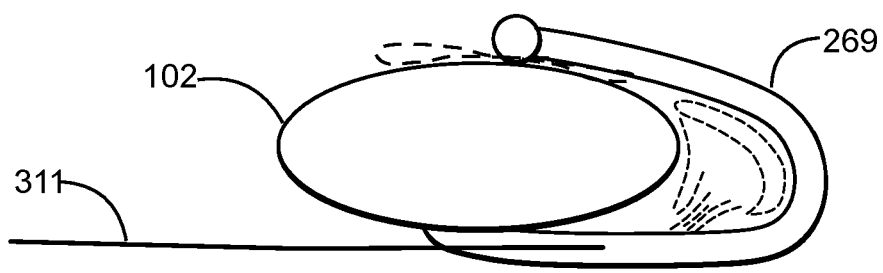

FIG. 14(a)-(c) is a series of illustration showing capture of the native tissue by the extendable self-contracting tab. FIG. 14(a) shows part 1 of a sequence of a distal tab tracking over the guide wire. FIG. 14(b) shows part 2 of a sequence showing withdrawal of the guide wire and self-contracting curvature of the distal tab.

FIG. 14(c) shows the distal tab pulling the native tissue against the outer wall of the prosthetic valve. FIG. 14(d) shows completed capture of the native tissue and anchoring of the valve.

Figure 15:
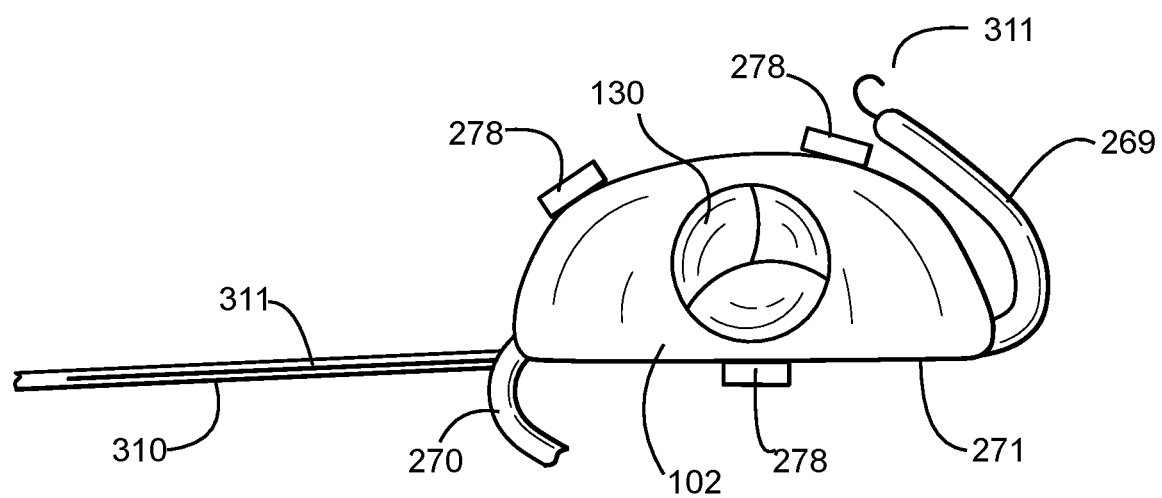

FIG. 15 is an illustration of a TOP view of a side-deliverable valve having the distal tab/securement arm, and additional anchoring elements.

Figure 16:
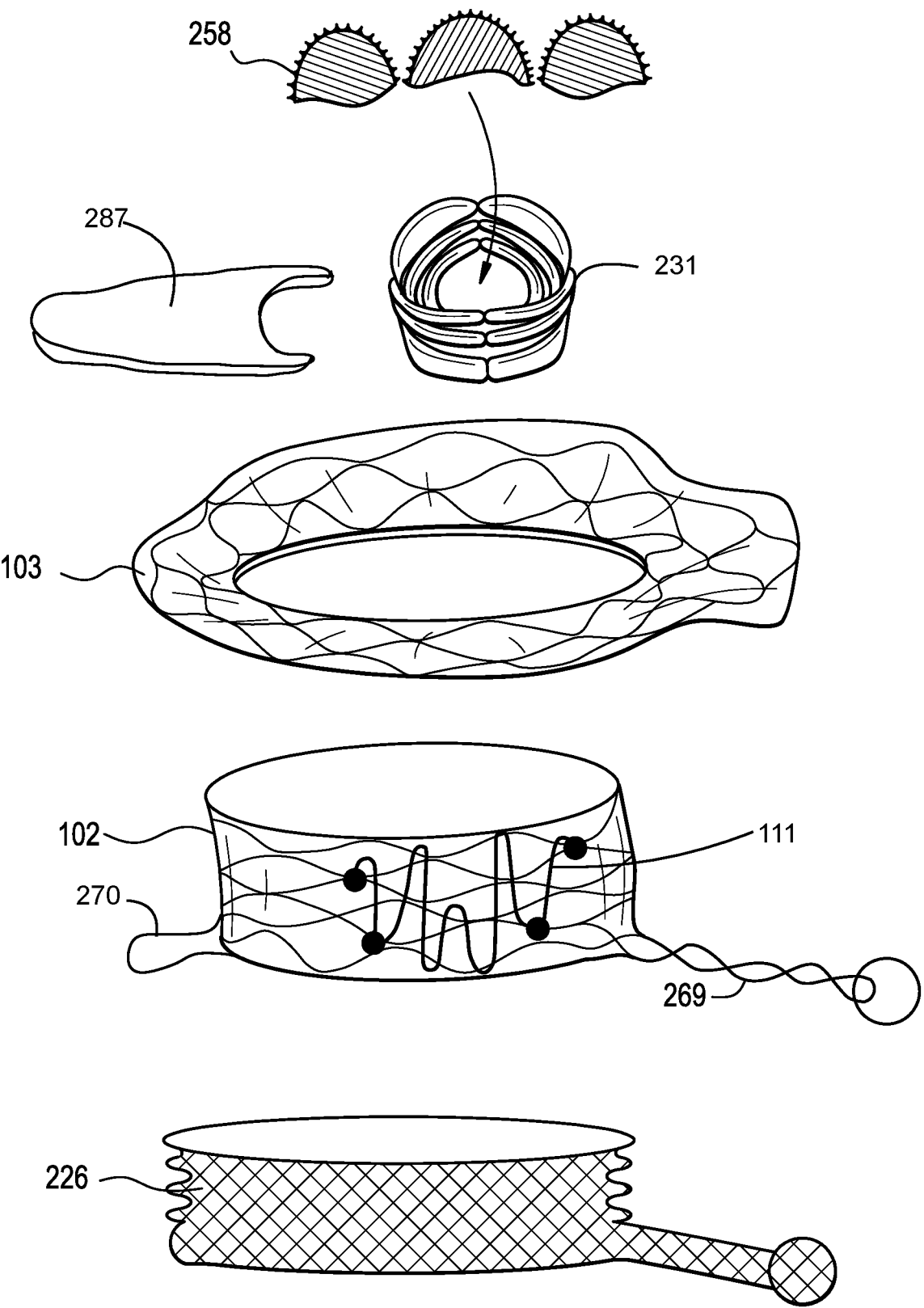

FIG. 16 is an illustration of a SIDE PERSPECTIVE view of an exploded view of an embodiment having three leaflet cusp or pockets mounted within a foldable and compressible inner wire frame, the inner is mounted within an outer wire frame which has a collar component attached circumferentially at a top edge of the outer wire frame, an integrated A2 clip, a distal tab component, and a mesh component, according to the invention.

Figure 17:
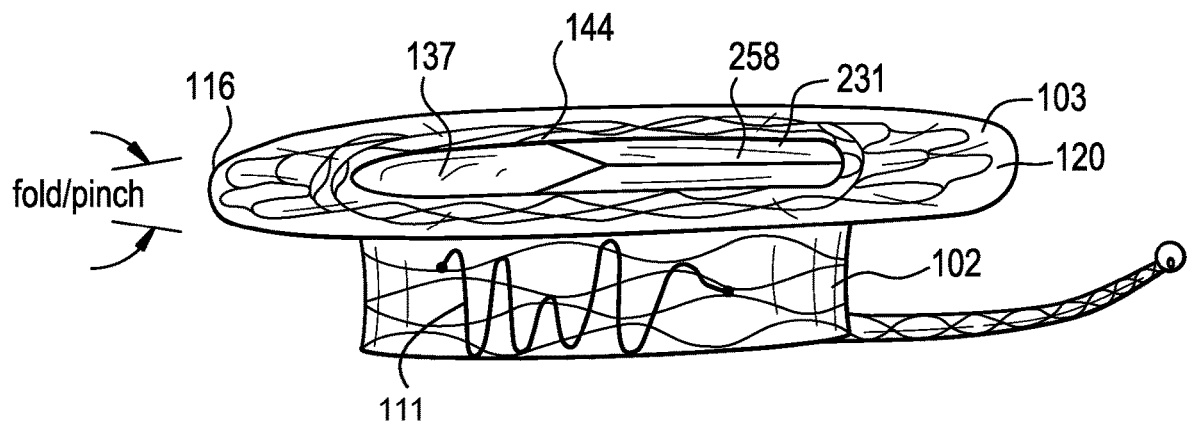

FIG. 17 is an illustration of a SIDE PERSPECTIVE view of a side deliverable transcatheter heart valve with an integrated A2 clip in a folded configuration along the z-axis (front to back when viewed from the broader side) according to the invention.

Figure 18:
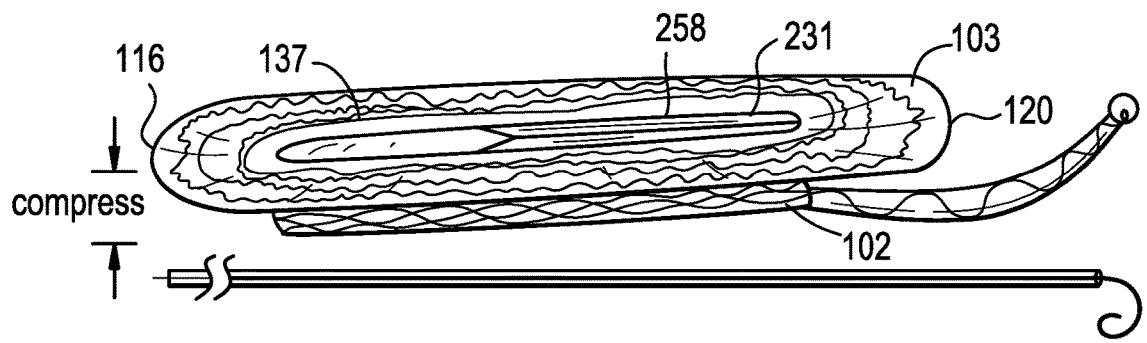

FIG. 18 is an illustration of a SIDE PERSPECTIVE view of a side deliverable transcatheter heart valve in a vertically compressed configuration according to the invention.

Figure 19:
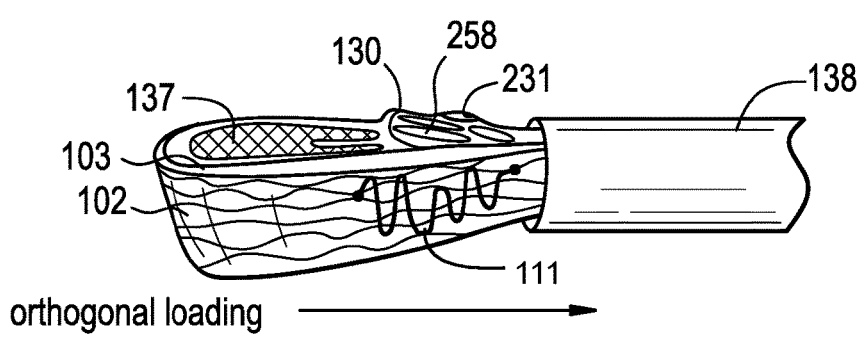

FIG. 19 is an illustration of a SIDE PERSPECTIVE view of a side deliverable transcatheter heart valve with an integrated A2 clip, partially loaded into a delivery catheter, according to the invention.

Figure 20:
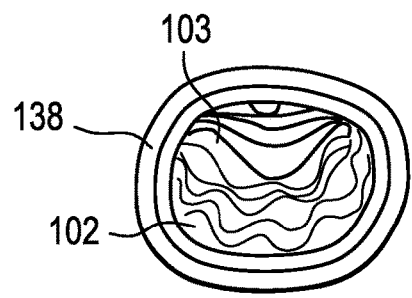

FIG. 20 is an illustration of an END view of a delivery catheter showing the loaded valve, according to the invention.

Figure 21:
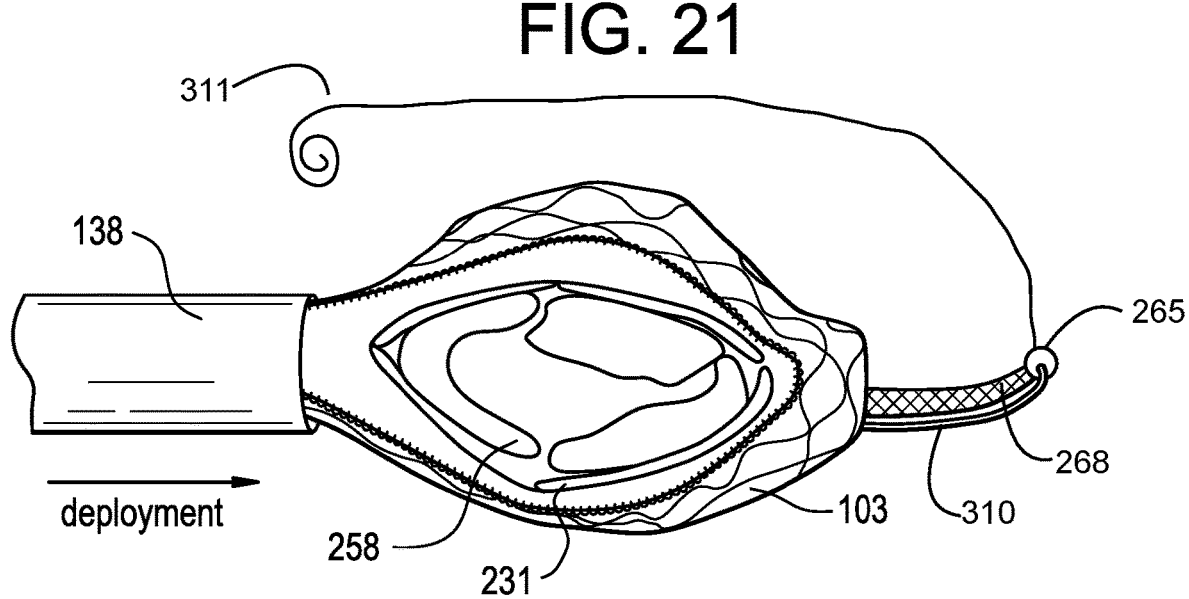

FIG. 21 is an illustration of a TOP view of the folded, compressed valve being expelled from the delivery catheter, in a partial position to allow expansion of the leaflets and the inner frame prior to seating in the native annulus.

Figure 22:
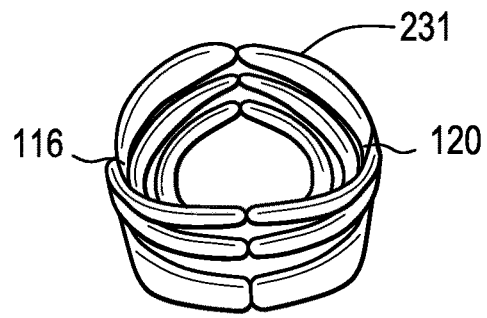

FIG. 22 is an illustration of a TOP PERSPECTIVE view of an inner leaflet frame in a cylinder configuration, shown at the beginning of a process permitting folding and compression of the inner frame, according to the invention.

Figure 23:
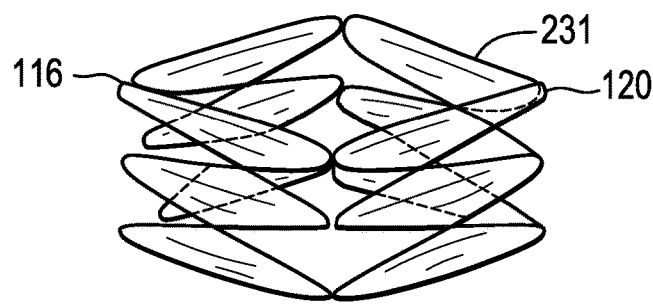

FIG. 23 is an illustration of a TOP PERSPECTIVE view of an inner leaflet frame in a partially folded configuration with the wireframe sidewalls rotating or hinging at their lateral connection points, shown as a partial first step in a process permitting folding and compression of the inner frame, according to the invention.

Figure 24:
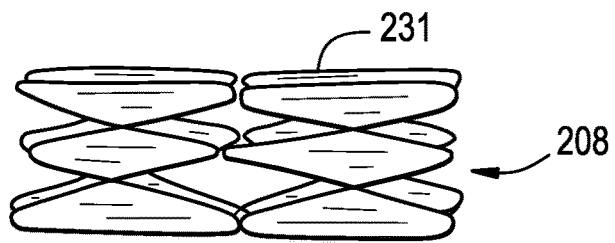

FIG. 24 is an illustration of a SIDE view of an inner leaflet frame in a completely folded configuration with the wireframe sidewalls rotated or hinged at their lateral connection points, shown as a completed first step in a process permitting folding and compression of the inner frame, according to the invention.

Figure 25:
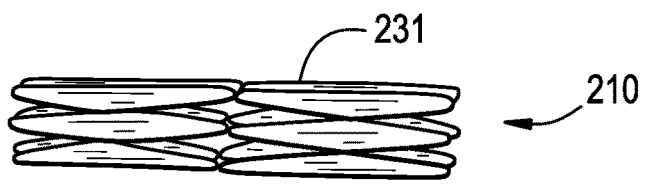

FIG. 25 is an illustration of a SIDE view of an inner leaflet frame in a folded and vertically compressed configuration with the wireframe sidewalls vertically compressed in a pleated or accordion configuration, shown as a second step in a process permitting folding and compression of the inner frame, according to the invention.

Figure 26:
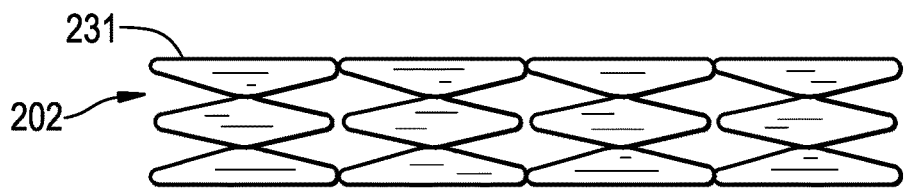

FIG. 26 is an illustration of a SIDE view of an inner leaflet frame as a linear wireframe sheet before further assembly into a cylinder structure, according to the invention.

Figure 27:
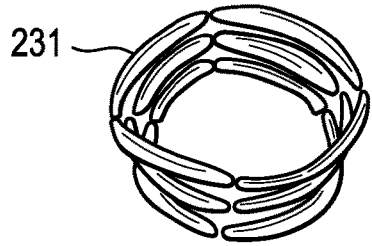

FIG. 27 is an illustration of a SIDE PERSPECTIVE view of an inner leaflet frame in a cylinder or cylinder-like (conical, etc) configuration, according to the invention.

Figure 28:
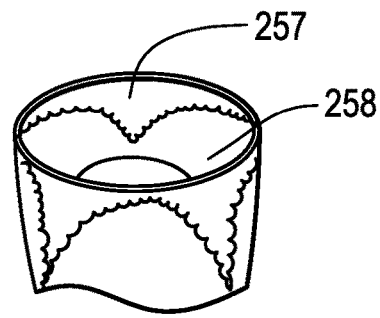

FIG. 28 is an illustration of a SIDE PERSPECTIVE view of a band of percardial tissue that is configured in a cylinder shape with leaflet pockets sewn into a structural band, according to the invention.

Figure 29:

FIG. 29 is an illustration of a SIDE view of a band of percardial tissue with leaflet pockets sewn into a structural band, before assembly into a cylindrical leaflet component and mounting on an inner frame to form a collapsible (foldable, compressible) flow control component, according to the invention.

Figure 30:
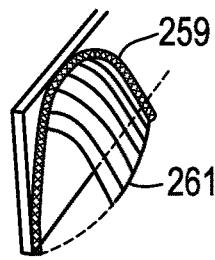

FIG. 30 is an illustration of a BOTTOM view of a band of percardial tissue with leaflet pockets sewn into a structural band, before assembly into a cylindrical leaflet component and mounting on an inner frame to form a collapsible (foldable, compressible) flow control component, according to the invention.

Figure 31:

FIG. 31 is an illustration of a SIDE PERSPECTIVE view of part of a band of percardial tissue with a single leaflet pocket sewn into a structural band, showing an open bottom edge and a sewn, closed top parabolic edge, according to the invention.

Figure 32:
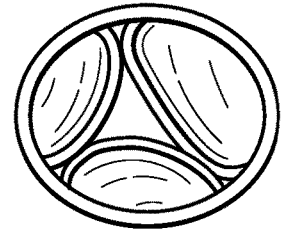

FIG. 32 is an illustration of a BOTTOM view of a cylindrical leaflet component showing partial coaptation of the leaflets to form a closed fluid-seal, according to the invention.

Figure 33:
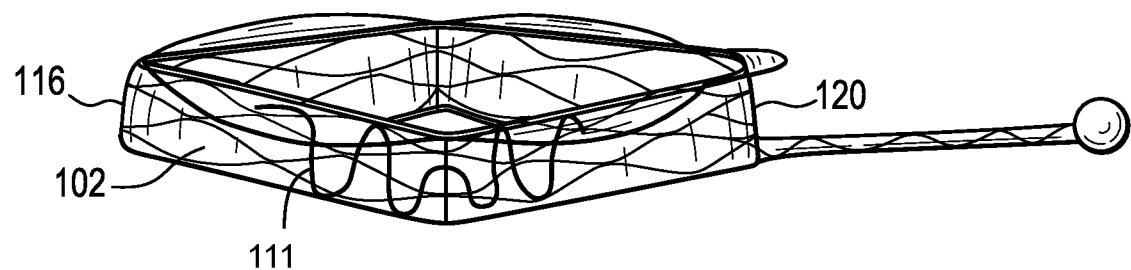

FIG. 33 is an illustration of a TOP PERSPECTIVE view of an outer frame with an integrated A2 clip in a partially folded configuration with the wireframe sidewalls rotating or hinging at their lateral connection points, shown as a partial first step in a process permitting folding and compression of the inner frame, according to the invention.

Figure 34:
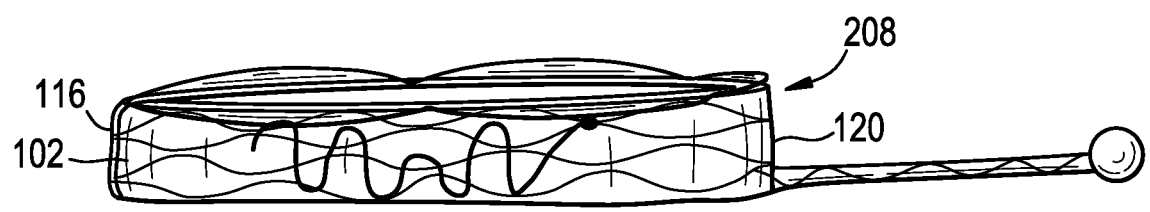

FIG. 34 is an illustration of a SIDE view of an outer frame with an integrated A2 clip in a completely folded flat configuration with the wireframe sidewalls rotated or hinged at their lateral connection points, shown as a completed first step in a process permitting folding and compression of the inner frame, according to the invention.

Figure 35:
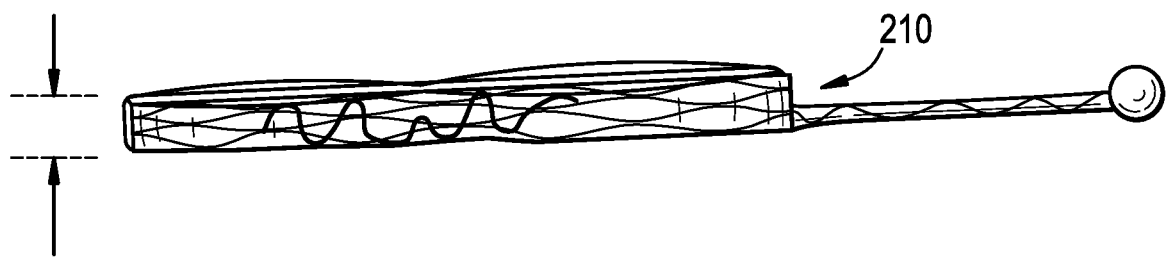

FIG. 35 is an illustration of a SIDE view of an outer frame with an integrated A2 clip in a folded and vertically compressed configuration with the wireframe sidewalls vertically compressed in a pleated or accordion configuration, shown as a second step in a process permitting folding and compression of the inner frame, according to the invention.

Figure 36:
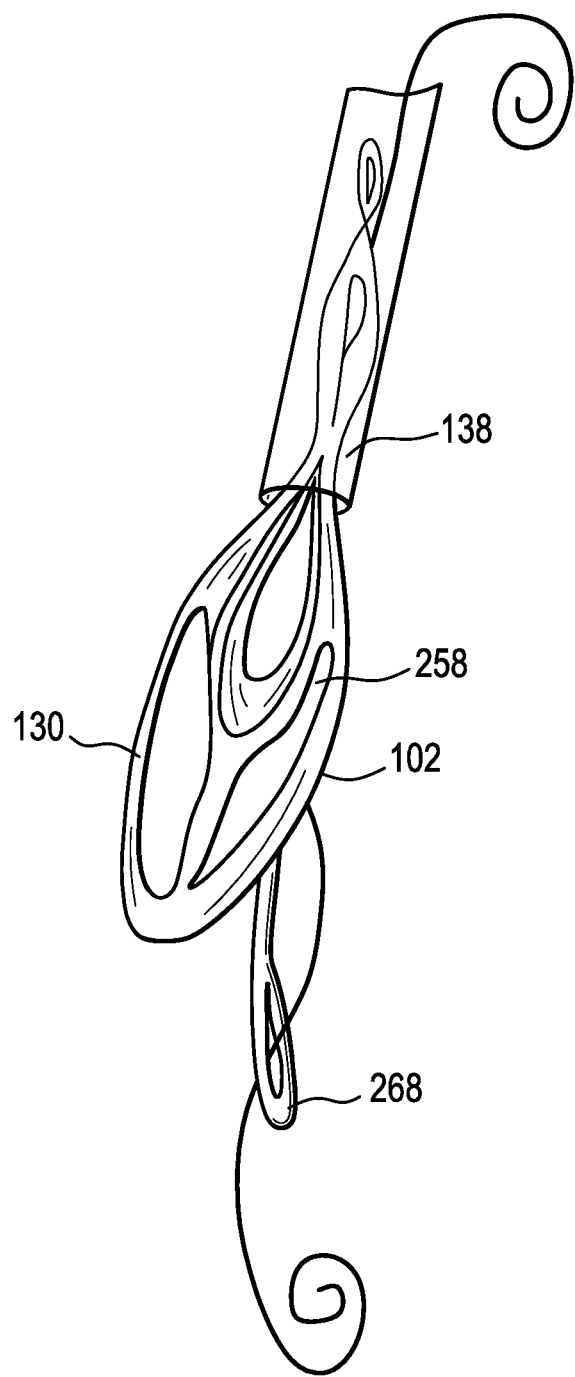

FIG. 36 is an illustration of a TOP view of a valve partially expelled from a delivery catheter, with a distal tab leading the valve (along guide wire not shown) to the deployment location, with distal flow control component beginning to open and showing two of three leaflets opening from a folded, lie-flat configuration with the third leaflet opening from a folded configuration where it is folded back on itself when in the delivery catheter, according to the invention.

Figure 37:
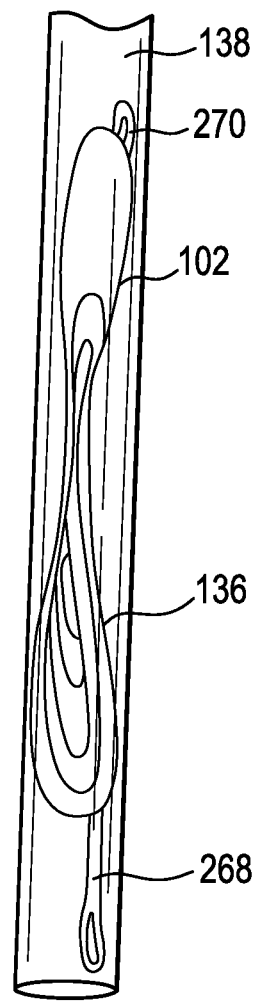

FIG. 37 is an illustration of a TOP view of a valve compressed (orthogonally loaded, or loaded for side-delivery) within a delivery catheter with a first tab extending forward along a x-axis and a second trailing tab extending backwards along the x-axis, according to the invention.

Figure 38:
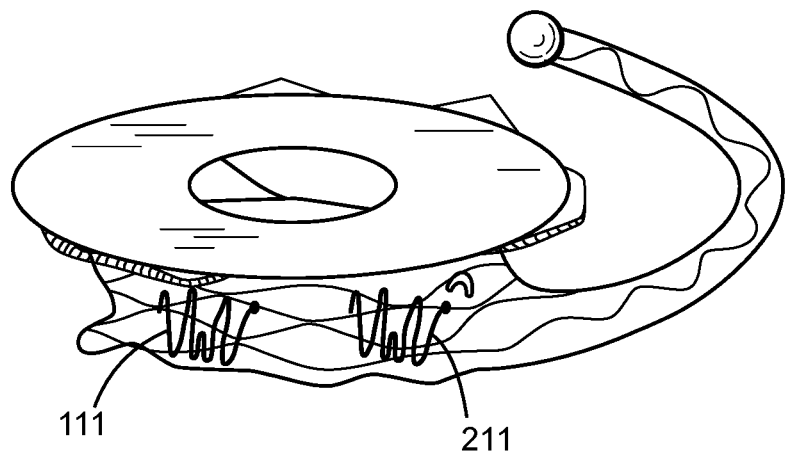

FIG. 38 is an illustration of an embodiment having multiple anterior side extendable clips mounted on the anterior-facing perimeter sidewall of the outer frame.

Figure 39:
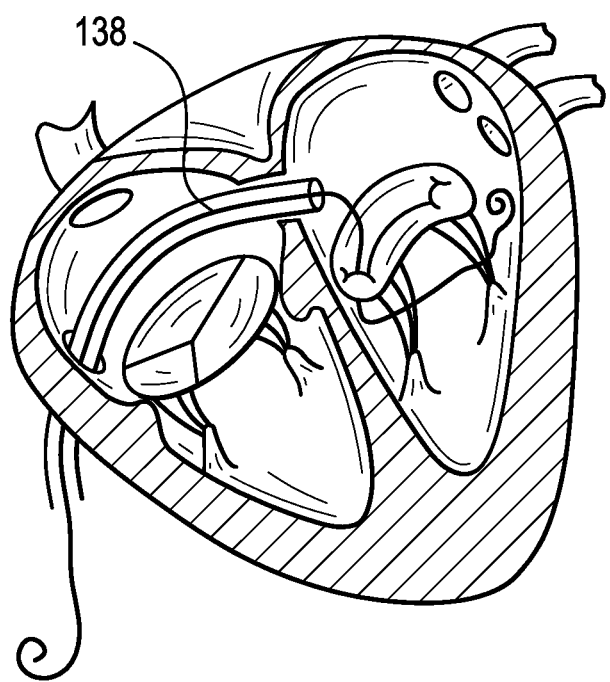
Figure 40:
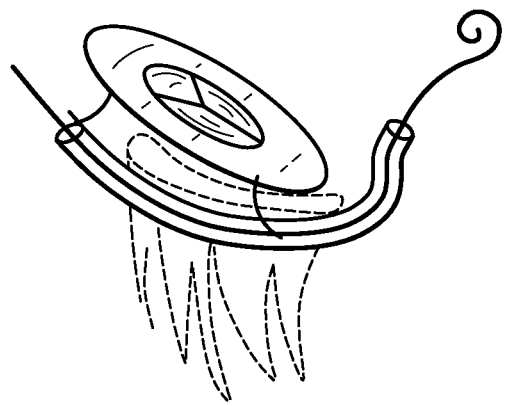

FIG. 39 is an illustration showing a process of using a distal tab and an A2 clip to capture native tissue, according to the invention.

DETAILED DESCRIPTION OF THE INVENTION

The invention is directed to a dual-tab transcatheter heart valve replacement that is a low profile, side delivered implantable prosthetic heart valve having an ring-shaped or annular support frame, an inner 2- or 3-panel sleeve, and an elongated sub-annular distal anchoring tab extending around and capturing the posterior leaflet.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Side-Delivery or Orthogonal Delivery

In the description and claims herein, the terms "side-delivered", "side-delivery", "orthogonal", "orthogonally delivered" and so forth are used to describe that the valves of the present invention are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Traditional valves have a central cylinder axis that is parallel to the length-wise axis of the delivery catheter and are deployed from the end of the delivery catheter and expanded radially outward from the central annular axis, in a manner akin to pushing a closed spring-loaded umbrella out of a sleeve to make it spring open. However, the valves of the present invention are compressed and delivered in a sideways manner. To begin with the shape of the expanded valve is that of a large diameter shortened cylinder with an extended collar or cuff. The valves are compressed, in one preferred embodiment, where the central axis of the valve is roughly perpendicular to (orthogonal to) the length-wise axis of the delivery catheter. In one preferred embodiment, the valves are compressed vertically, similar to collapsing the height of a cylinder accordion-style from taller to shorter, and the valves are also compressed by folding a front panel against a back panel. In another preferred embodiment, the valves may be compressed by rolling.

Traditional valves can only be expanded as large as what the internal diameter of the delivery catheter will allow. Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, eg. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In preferred embodiments of the invention, the transcatheter approach includes (i) advancing to the mitral valve or pulmonary artery of the heart through the inferior vena cava via the femoral vein, (ii) advancing to the mitral valve or pulmonary artery of the heart through the superior vena cava via the jugular vein, (iii) advancing to the mitral valve of the heart through a trans-atrial approach, e.g. fossa ovalis or lower, via the IVC-femoral or the SVC-jugular approach.

Annular Support Frame

In the description and claims herein, the term "annular support frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the the back wall portion can be further defined as having a back upper collar portion and a back lower body portion.

The annular (outer) support frame has a flow control component mounted within the annular support frame and configured to permit blood flow in a first direction through an inflow end of the valve and block blood flow in a second direction, opposite the first direction, through an outflow end of the valve.

Since the outer frame is preferably made of superelastic metal or alloy such as Nitinol, the frame is compressible. Preferably, the outer frame is constructed of a plurality of compressible wire cells having a orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In one preferred embodiment, the annular support frame used in the prosthetic heart valve deployed in the mitral annulus may have a complex shape determined by the anatomical structures where the valve is being mounted. For example, in the mitral annulus, the circumference of the mitral valve may be a rounded ellipse, the septal wall is known to be substantially vertical, and the mitral is known to enlarge in disease states. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of—, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution.

Ejection fraction is a measurement of the percentage of blood leaving your heart each time it contracts. During each heartbeat pumping cycle, the heart contracts and relaxes. When your heart contracts, it ejects blood from the two pumping chambers (ventricles).

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine)

(Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic mitral valves, and bioprosthetic pulmonary valves.

Tethers—

The tethers are made from surgical-grade materials such as biocompatible polymer suture material. Non-limiting examples of such material include ultra high-molecular weight polyethylene (UHMWPE), 2-0 exPFTE(polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic heart valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.
Polyurethanes Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.
Covered Wire Frame Materials Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the valve include the following details and features.
Example The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In a preferred embodiment the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the mitral annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native mitral valve.
Example—Manufacturing Process In a preferred embodiment the invention includes a process for manufacturing a side-delivered transcatheter prosthetic heart valve frame, comprising:
  (i) using additive or subtractive metal or metal-alloy manufacturing to produce
  a self-expanding annular support frame,
  wherein the additive metal or metal-alloy manufacturing is 3D printing or direct metal laser sintering (powder melt), and
  wherein the subtractive metal or metal-alloy manufacturing is photolithography, laser sintering/cutting, CNC machining, electrical discharge machining.

Figure 1:
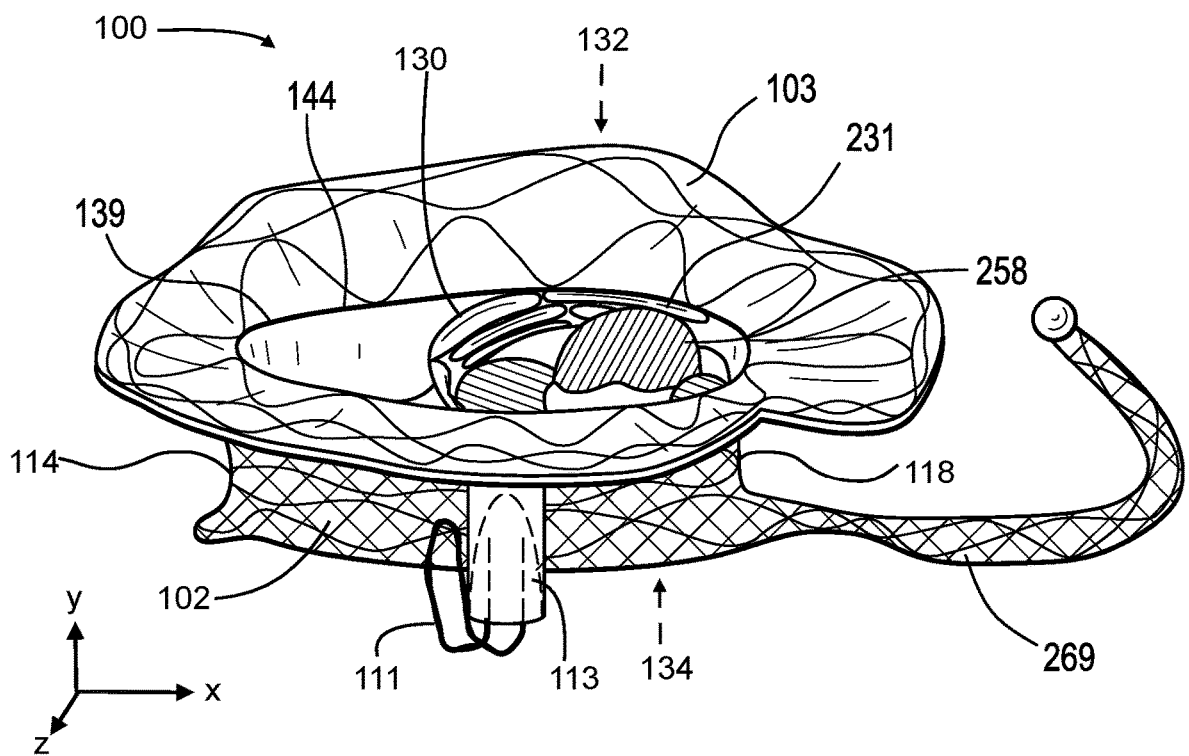

In another preferred embodiment, there is provided a process for manufacturing a side-delivered transcatheter prosthetic heart valve frame, further comprising the steps of:
(ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.
Example—Compression Methods In another preferred embodiment, there is provided a method of compressing, wherein the implantable prosthetic heart valve is rolled or folded into a compressed configuration using a step selected from the group consisting of:
(i) unilaterally rolling into a compressed configuration from one side of the annular support frame;
(ii) bilaterally rolling into a compressed configuration from two opposing sides of the annular support frame;
(iii) flattening the annular support frame into two parallel panels that are substantially parallel to the long-axis, and then rolling the flattened annular support frame into a compressed configuration; and
(iv) flattening the annular support frame along a vertical axis to reduce a vertical dimension of the valve from top to bottom.
Drawings Referring now to the drawings, FIG. 1 is an illustration of a SIDE PERSPECTIVE view of a side-delivered (orthogonally deliverable) transcatheter heart valve 100 with an A2 clip 111 and an extendable self-contracting distal anchoring tab 269. A2 clip 111 is vertically extended subannularly during deployment of the valve to capture native leaflet, e.g. A2, tissue, when the A2 clip 111 is retracted. The A2 clip is actuated using a steerable catheter and/or guidewire system to deliver an external A2 clip 111 or to extend a pre-existing sheathed A2 clip from a mesh pocket on the sidewall of the valve body. When an external A2 clip 111 is delivered, imaging markers on or around the sleeve/pocket/sheath 113 help guide the steerable catheter to the A2 clip sleeve/pocket/sheath 113, where the A2 clip 111 is pushed to a subannular position, then a catheter sheath is withdrawn to expose a distal portion of the A2 clip and expand the distal portion to a shape-memory (spring-effect) configuration. When the expanded distal portion of the A2 clip 111 is pulled up atrially in the direction of the underside of the native annulus, the expanded distal portion captures the native leaflet (A2 or other desired leaflet) and secures it against the underside of the annulus and/or valve body.

Distal anchoring tab 269 tracks on a guide wire inserted near the A1 leaflet/commissure of the mitral valve. The guide wire is pre-positioned around the native mitral leaflets and/or chordae, especially the mitral P2 leaflet, to facilitate the over-wire placement of the distal anchoring tab 269 around the "back side" of the P2 leaflet to clamp the native P2 leaflet against the frame 102.

The use of an A2 clip on one side (A2) and a wrap-around distal tab 269 on an opposite side (P2) provides oppositional anchoring and securement and can reduce micro-motion and encourage in-growth success of the valve.

FIG. 1 also shows collapsible flow control component 130 mounted within the annular outer support frame 102, the collapsible (inner) flow control component 130 having leaflet frame 231 with 2-4 flexible leaflets 258 mounted thereon, the leaflet frame 231 foldable on an z-axis (front-to-back) 109 from a cylindrical configuration to a flattened cylinder configuration and compressible along a vertical axis 108 (y-axis) to a shortened configuration, according to the invention. FIGS. 33-35 provide one exemplary illustration.

Like the inner leaflet frame, the annular outer support frame 102, 103 is made from a shape-memory material such as Nickel-Titanium alloy, for example NiTiNOL, and is therefore a self-expanding structure starting from a compressed configuration. The annular (outer) support frame 102, 103 has a central (interior) channel and an outer perimeter wall circumscribing a central vertical axis 108, when in an expanded configuration, and said annular outer support frame 102 having a distal side 118 and a proximal side 114.

The flow control component 130 is mounted within the annular outer support frame 102 and is configured to permit blood flow in a first direction, e.g. atrial to ventricular, through an inflow end 132 of the valve 100 and block blood flow in a second direction, opposite the first direction, through an outflow end 134 of the valve 100.

The inner flow control component 130, like the outer annular frame 102, is foldable and compressible. The inner flow control component 130 comprises leaflet frame 231 with 2-4 flexible leaflets 258 mounted on the leaflet frame 231.

The flow control component 130, and thereby the leaflet frame 231, like the outer frame 102, is foldable along a z-axis (front to back) from a cylindrical configuration to a flattened cylinder configuration, where the fold lines are located on a distal side and on a proximal side, taking the leaflet frame 231 from a ring or cylinder shape, and flattening it from a ring to a two-layer band i.e. folded over on itself, or like a cylinder flattened into a rectangle or square joined along two opposing sides. This allows the outer frame 102 and the flow control component 130 to reduce the radius along z-axis until the side walls are in contact or nearly so. This also allows the outer frame 102 and the flow control component 130 to maintain the radius along the horizontal axis, the y-axis, to minimize the number of wire cells, which make up the outer and the inner, that are damaged by forces applied during folding and/or compression necessary for loading into the delivery catheter.

The flow control component 130, leaflet frame 231, and the outer frame 102 are also vertically (y-axis) compressible, reducing the height of the entire valve structure to fit within the inner diameter of a 24-36 Fr (8-12 mm inner diameter) delivery catheter 138 (not shown in this Figure). By folding and compressing in the z-axis and vertically compressing in the y-axis, the valve structure is permitted to maintain a very large dimension, for example, 40-80 mm along the horizontal, or x-axis. For example, a 60 mm or larger diameter valve can be delivered via transcatheter techniques. The length of the long axis of a valve, e.g. 60 mm, since it runs parallel to the central axis of the delivery catheter, is not limited by the large amount of wire frame and cover material necessary for such a large valve. This is not possible with existing center-axis delivery (axial) transcatheter valves. The use of a folded, compressed valve that is orthogonal to the traditional axial-delivery valves permits treatment options not available previously.

FIG. 1 also shows extendable self-contracting distal anchoring tab 269 mounted on the distal side 118 of the annular outer support frame 102.

In a preferred embodiment, the horizontal x-axis of the valve is orthogonal to (90 degrees), or substantially orthogonal to (75-105 degrees), or substantially oblique to (45-135 degrees) to the central vertical y-axis when in an expanded configuration.

In a preferred embodiment, the horizontal x-axis of the compressed configuration of the valve is substantially parallel to a length-wise cylindrical axis of the delivery catheter.

In another preferred embodiment, the valve has a compressed height (y-axis) and width (z-axis) of 6-15 mm, preferably 8-12 mm, and more preferably 9-10 mm, and an expanded deployed height of about 5-60 mm, preferably about 5-30 mm, and more preferably about 5-20 mm or even 8-12 mm or 8-10 mm. It is contemplated in preferred embodiments that the length of the valve, x-axis, does not require compression since it can extend along the length of the central cylindrical axis of the delivery catheter.

In a preferred embodiment, the valve has an expanded diameter length and width of 25-80 mm, preferably 40-80 mm, and in certain embodiments length and/or width may vary and include lengths of 25 mm, 30 mm, 35 mm, 40 mm, 45 mm, 50 mm, 55 mm, 60 mm, 65 mm, 70 mm, 75 mm, and 80 mm, in combination with widths that are the same or different as the length.

In certain preferred embodiments, the valve is centric, or radially symmetrical. In other preferred embodiments, the valve is eccentric, or radially (y-axis) asymmetrical. In some eccentric embodiments, the frame 102 may have a D-shape in cross-section so the flat portion can be matched to the mitral annulus near the anterior leaflet.

In certain preferred embodiments, the inner frame 231 is 25-29 mm in diameter, the outer frame 102 is 50-70 mm in diameter, and the collar structure 103 extends beyond the top edge of the outer frame by 10-30 mm to provide a seal on the atrial floor against perivalvular leaks (PVLs).

Atrial collar 103 is shaped to conform to the native deployment location. In a mitral replacement, the atrial collar will be configured with varying portions to conform to the native valve. In one preferred embodiment, the collar will have a distal and proximal upper collar portion. The distal collar portion can be larger than the proximal upper collar portion to account for annular or subannular geometries.

Figure 2:
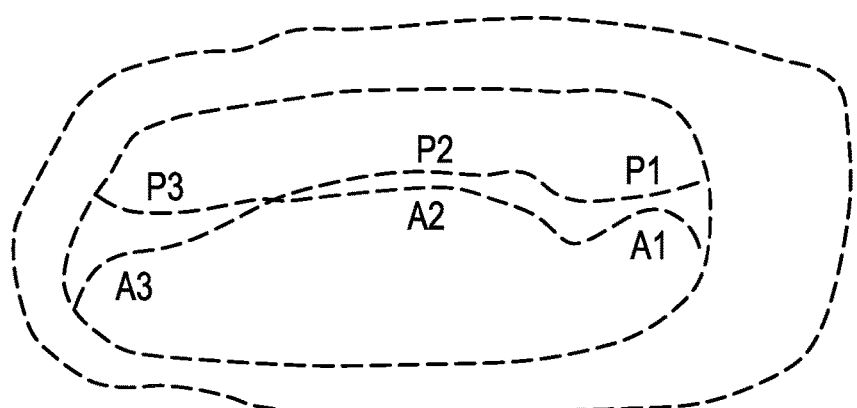
FIG. 2 is an illustration of a top view of a native mitral valve showing approximate locations of leaflet areas A1-A2-A3 and P1-P2-P3.

FIG. 2 is an illustration of a top view of a native mitral valve showing approximate locations of leaflet areas A1-A2-A3 and P1-P2-P3.

Figure 3:
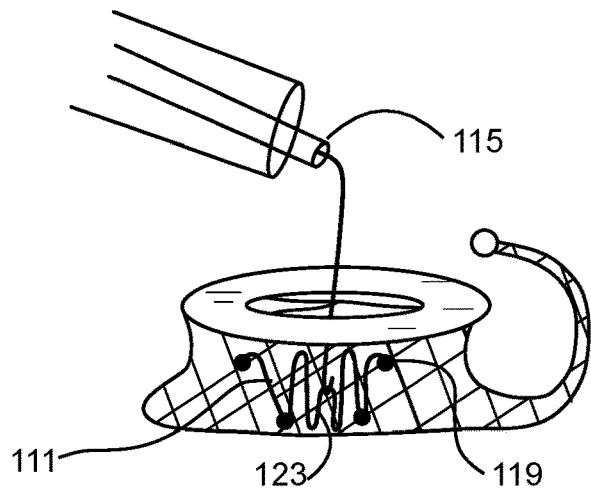
FIG. 3 is an illustration of a side perspective view of a valve having an A2 clip in the folded position.

FIG. 3 is an illustration of a side perspective view of a valve having an A2 clip 111 in the folded position. Steerable catheter/guidewire 115 is shown deploying this shape-memory pre-installed "wire-W" embodiment of the A2 clip 111. A2 clip attachment points 119 secure a proximal portion of the A2 clip so that extendable hook portion 123 can be extended and retracted.

Figure 4:
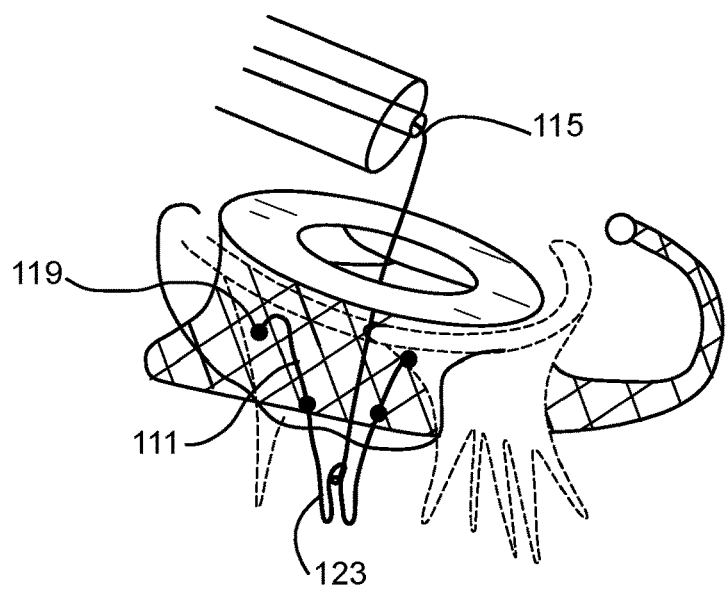
FIG. 4 is an illustration of a side perspective view of a valve having an A2 clip in the extended position.

FIG. 4 is an illustration of a side perspective view of a valve having an A2 clip 111 in the extended position. Steerable catheter/guidewire 115 is shown deploying this shape-memory pre-installed "wire-W" embodiment of the A2 clip 111 to a sub-annular position to capture leaflet tissue. A2 clip attachment points 119 secure a proximal portion of the A2 clip so that when extendable hook portion 123 is extended, it generates a spring-back force to capture the tissue caught between the A2 clip and the annulus and/or valve body.

Figure 5:
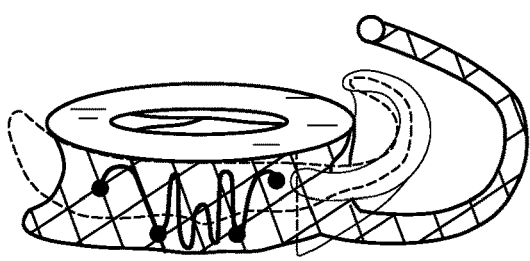
FIG. 5 is an illustration of a side perspective view of a valve having an A2 clip in the re-folded position after capturing anterior leaflet and/or chordae tissue, especially the A2 leaflet.

FIG. 5 is an illustration of a side perspective view of a valve having an A2 clip 111 in the re-folded position after capturing anterior leaflet and/or chordae tissue, especially the A2 leaflet.

FIG. 6 (a)-(d) is an illustration of an A2 clip in a pocket or sleeve 113 that would be mounted on the perimeter wall of the outer frame. FIG. 6(a) shows an A2 clip, post-hook embodiment 223, stowed in the pocket 113 before deployment. Clip attachment 119 is shown adjacent the clip 223 with upper portion of the clip 225 in a compressed, folded configuration.

Figure 6A:
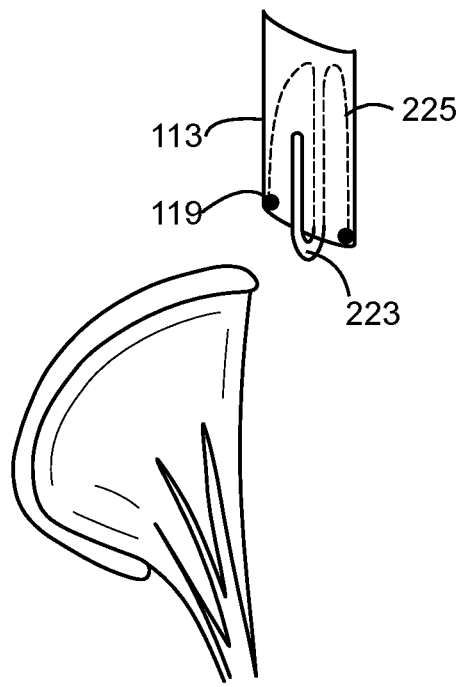
Figure 6B:
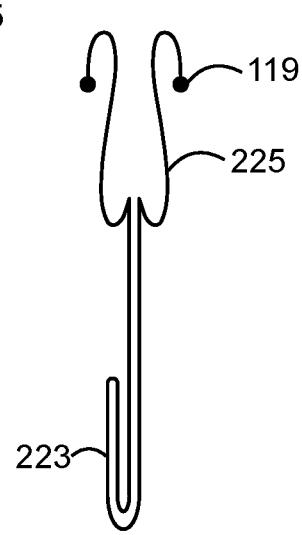

FIG. 6(b) shows an A2 clip extended in a ventricular direction along the central (y) axis. FIG. 6(b) shows attachment points 119 positioned above the upper proximal portion 225 of the clip. Post-type hook 223 is shown folded and unextended in a sub-annular position.

Figure 6C:
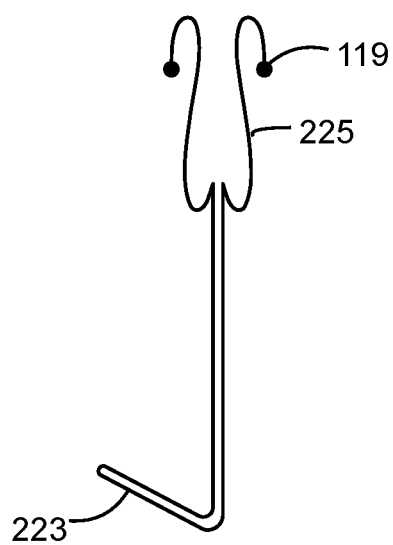

FIG. 6(c) shows an A2 clip completely unfolded for capturing anterior tissue. FIG. 6(c) shows extended configuration with attachment points 119 positioned above the upper proximal portion 225 of the clip. Post-type hook 223 is shown unfolded and extended in a sub-annular position to capture native tissue.

Figure 6D:
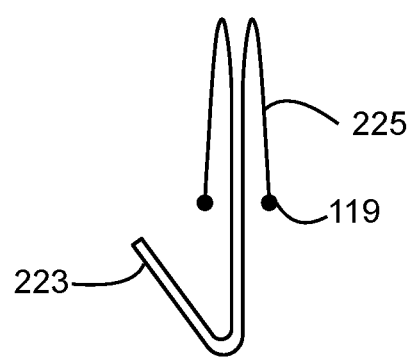

FIG. 6(d) shows a retracted, re-folded A2 clip in a position after capture of tissue where the tissue (not shown) is pinned against the perimeter wall of the outer frame. In a retracted position, FIG. 6(d) shows attachment points 119 positioned again below the upper proximal portion 225 of the clip, while post-type hook 223 is shown unfolded and extended in a capturing configuration.

Figure 7A:
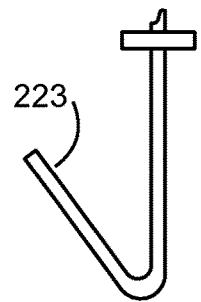
Figure 7B:
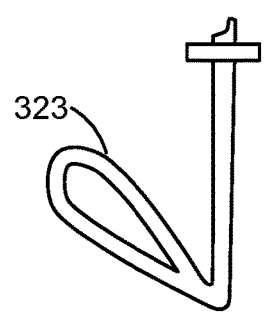
Figure 7C:
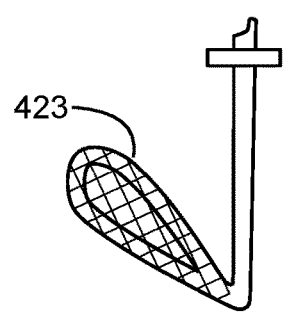
Figure 7D:
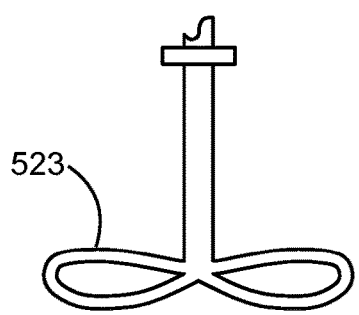
Figure 7E:
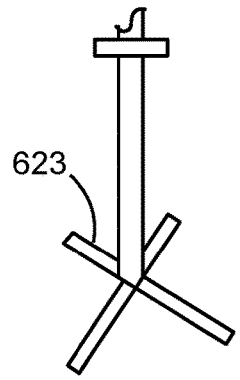
Figure 7F:
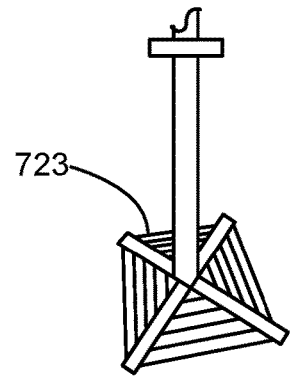
Figure 7G:
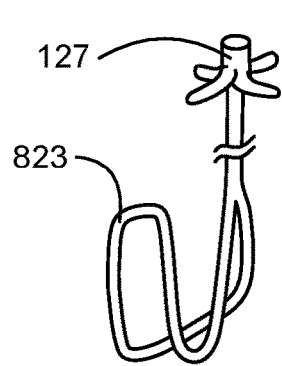
Figure 7H:
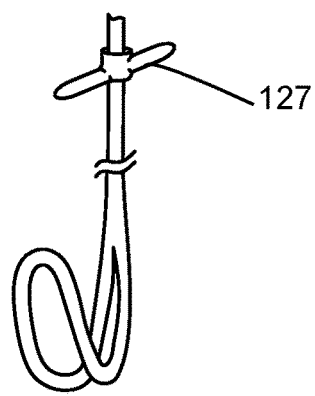

FIG. 7(a)-(h) is an illustration of a variety of anchor loop configurations contemplated for use as a distal portion of the A2 clip. FIG. 7(a) shows a post-type hook 223. FIG. 7(b) shows a loop-type hook 323. FIG. 7(c) shows a paddle-type hook 423. FIG. 7(d) shows a double loop-type hook 523. FIG. 7(e) shows a footer-type hook 623. FIG. 7(f) shows a fish trap-type hook 723. FIG. 7(g) shows a bent loop-type hook 823. FIGS. 7(g) and 7(h) also show use of an optional locking nut 127 for an A2 clip.

FIG. 8 is an illustration of a TOP view of a mitral valve and shows guide wire 434 directing the replacement valve 100 to the A1 leaflet with the valve 100 in a compressed intra-catheter configuration, according to the invention. Distal tab 268 is shown with guide wire 434 threaded through the end of the distal tab 268, to guide the distal tab 268 is over the guide wire 434, and lead the valve 100 into the correct deployment location.

FIG. 9 is an illustration of a TOP view of a mitral valve and prosthetic valve 100 with distal tab 268 attached to the outer frame 102 and guide wire 434 threaded through the end of the distal tab 268, such that when the guide wire 434 is pre-positioned into the A1 location, the distal tab 268 is fed over the guide wire 434 leading the valve 100 into the correct deployment location. The valve 100 is in a partial deployment stage being partially expelled from delivery catheter 138, according to the invention.

FIG. 10 is an illustration of a TOP PERSPECTIVE view of a prosthetic valve 100 having collar 103, outer frame 102, inner frame 231, and spacer component 137. Distal tab 268 is attached to the outer frame 102 and guide wire 434 is threaded through the end of the distal tab 268, such that when the guide wire 434 is pre-positioned into the A1 location, the distal tab 268 is fed over the guide wire 434 leading the valve 100 into the correct deployment location. FIG. 80 shows the valve 100 fully expelled from delivery catheter 138 and positioned temporarily at an upwards angle with a distal anchoring tab 268 in the A1 area. This angled positioning avoids a pop-off effect and allows for the new prosthetic valve 100 to engage the blood flow while the native mitral valve continues to operate, just prior to the proximal side being shoe-horned into place for a non-traumatic transition from native valve to prosthetic valve 100, according to the invention.

FIG. 11 is an illustration of a TOP view of a prosthetic valve deployed in the native annulus (not visible—in dashed line), according to the invention.

FIG. 12 is an illustration of a SIDE PERSPECTIVE view of a prosthetic valve with an extended integrated A2 clip 111, deployed in the native annulus (not visible), according to the invention.

FIG. 13 is an illustration of a SIDE PERSPECTIVE view of an embodiment of a prosthetic valve having a retracted A2 clip 111 integrated into the sidewall 110 of the A2 facing side of the outer frame 102 of the valve, according to the invention.

FIG. 14(a)-(d) is a series of illustration showing capture of the native tissue by the extendable self-contracting tab 269. FIG. 14(a) shows part 1 of a sequence of a distal tab 269 tracking over the guide wire 311. FIG. 14(b) shows part 2 of a sequence showing withdrawal of the guide wire 311 and self-contracting curvature of the shape-memory distal tab 269. FIG. 14(c) shows the distal tab 269 pulling the native tissue against the outer wall 102 of the prosthetic valve. FIG. 14(d) shows completed capture of the native tissue by tab 269 against side wall 102 and anchoring of the valve. The tab 269 resumes a pre-curved configuration as guide wire 311 is withdrawn.

FIG. 15 is an illustration of a TOP view of an orthogonal valve having the distal tab/securement arm 269, and additional anchoring elements 278. Catheter 310 has guidewire 311 disposed within the lumen of the catheter. Proximal tab 270 is used to anchor the valve into or against native tissue on the proximal side. Flow control component 130 is shown with three (3) leaflets and is centrally positioned within the outer frame of a D-shaped 271 valve.

FIG. 16 is an illustration of a SIDE PERSPECTIVE view of an exploded view of an embodiment having three leaflet cusp or pockets 258 mounted within a foldable and compressible inner wire frame 231, the inner 231 is mounted within an outer wire frame 102 having a spacer panel 287. Outer frame 102 has a collar component 103 attached circumferentially at a top edge 107 of the outer wire frame Covered spacer 287 can be pierced to provide planned regurgitation and/or can be used to provide a conduit for pacer wires. Integrated anchoring A2 clip 111, and a distal anchoring tab component 269 provide subannular valve securement to provide an upward force against the underside of the native annulus, which opposes the downward force against the atrial floor and top of the native annulus that is provided by the collar component 103. Mesh component 226 provides a biocompatible covering (e.g. polyester) to facilitate and encourage in-growth, according to the invention.

Atrial collar 103 is shaped to conform to the native deployment location. In a mitral replacement, the atrial collar will have a tall back wall portion to conform to the septal area of the native valve, and will have a distal and proximal upper collar portion. The distal collar portion can be larger than the proximal upper collar portion to account for the larger flat space above (atrial) the left ventricular outflow tract (LVOT) subannular area.

Integrated tabs are unitary construction with the body of the outer frame. The tabs may vary in size and shape. In a preferred embodiment, the distal tab, e.g. 269 may be longer to reach posterior leaflet tissue and chordae. In above preferred embodiment, the shapes of the tabs are configured to conform to the A1 and A3 commissural areas of the mitral valve.

FIG. 17 is an illustration of a SIDE PERSPECTIVE view of a side deliverable transcatheter heart valve 100 with an integrated A2 clip 111 in a folded configuration along the z-axis (front to back when viewed from the broader side) according to the invention. FIG. 5 shows folded (flattened) outer frame 102 with folded/flattened collar 103, hinge points 116, 120. FIG. 5 also shows folded/flattened spacer 137, and leaflets 258 mounted within folded/flattened inner frame 231.

FIG. 18 is an illustration of a SIDE PERSPECTIVE view of a side deliverable transcatheter heart valve 100 with an integrated A2 clip in a vertically compressed configuration according to the invention. FIG. 6 shows outer frame 102 folded (z-axis) and compressed vertically (y-axis) with collar 103 folded (z-axis) and compressed (y-axis), along fold line between hinge points 116, 12o. FIG. 6 also shows spacer 137, and leaflets 258 mounted within inner frame 231.

FIG. 19 is an illustration of a SIDE PERSPECTIVE view of a side deliverable transcatheter heart valve 100 with an integrated A2 clip 111 partially loaded into a delivery catheter 138, according to the invention. FIG. 7 shows outer frame 102, A2 clip, folded collar 103, and flow control component 130 having leaflets 258 and an inner frame 231.

FIG. 20 is an illustration of an END view of a delivery catheter 138 showing the loaded valve 100 with outer frame 102 and collar 103 visible, according to the invention.

FIG. 21 is an illustration of a TOP view of the folded, compressed valve being expelled from the delivery catheter 138, in a partial position to allow expansion of the leaflets 258, collar 103, and the inner frame 231 prior to seating in the native annulus.

FIG. 22 is an illustration of a TOP PERSPECTIVE view of an inner leaflet frame 231 in a cylinder configuration, shown at the beginning of a process permitting folding and compression of the inner frame, according to the invention.

FIG. 23 is an illustration of a TOP PERSPECTIVE view of an inner leaflet frame 231 in a partially folded configuration with the wireframe sidewalls rotating or hinging at their lateral connection points 116, 120, shown as a partial first step in a process permitting folding and compression of the inner frame, according to the invention.

FIG. 24 is an illustration of a SIDE view of an inner leaflet frame 231 in a completely folded configuration 208 with the wireframe sidewalls rotated or hinged at their lateral connection points, shown as a completed first step in a process permitting folding and compression of the inner frame 231, according to the invention.

FIG. 25 is an illustration of a SIDE view of an inner leaflet frame 231 in a folded and vertically compressed configuration 210 with the wireframe sidewalls vertically compressed in a pleated or accordion configuration, shown as a second step in a process permitting folding and compression of the inner frame, according to the invention.

FIG. 26 is an illustration of a SIDE view of an inner leaflet frame 231 as a linear wireframe sheet 202 before further assembly into a cylinder structure, according to the invention.

FIG. 27 is an illustration of a SIDE PERSPECTIVE view of an inner leaflet frame 231 in a cylinder or cylinder-like (conical, etc) configuration, according to the invention.

FIG. 28 is an illustration of a SIDE PERSPECTIVE view of a band of percardial tissue 257 that is configured in a cylinder shape with leaflet pockets 258 sewn into a structural band 257, according to the invention.

FIG. 29 is an illustration of a SIDE view of a band of percardial tissue 257 with leaflet pockets sewn into a structural band 257, before assembly into a cylindrical leaflet component and mounting on an inner frame to form a collapsible (foldable, compressible) flow control component, according to the invention.

FIG. 30 is an illustration of a BOTTOM view of a band of percardial tissue 257 with leaflet pockets 258 sewn into a structural band 257, before assembly into a cylindrical leaflet component and mounting on an inner frame to form a collapsible (foldable, compressible) flow control component, according to the invention.

FIG. 31 is an illustration of a SIDE PERSPECTIVE view of part of a band of percardial tissue with a single leaflet pocket sewn into a structural band, showing partial coaptation of a leaflet pocket 258 with open edge 261 extending out and sewn edge 259 as closed top parabolic edge providing attachment, according to the invention.

FIG. 32 is an illustration of a BOTTOM view of a cylindrical leaflet component 258 showing complete coaptation, to form a closed fluid-seal, according to the invention.

FIG. 33 is an illustration of a TOP PERSPECTIVE view of a partially folded configuration of the outer wireframe 102 with an integrated A2 clip 111, with sidewalls rotating or hinging at their lateral connection points 116, 120, shown as a partial first step in a process permitting folding and compression of the outer frame 102, according to the invention.

FIG. 34 is an illustration of a SIDE view of an outer frame 102 with an integrated A2 clip in a completely folded flat configuration 208 with the wireframe sidewalls rotated or hinged at their lateral connection points 116, 120, shown as a completed first step in a process permitting folding and compression of the outer frame 102, according to the invention.

FIG. 35 is an illustration of a SIDE view of an outer frame 102 with an integrated A2 clip in a folded and vertically compressed configuration 210 with the wireframe sidewalls vertically compressed in a pleated or accordion configuration, shown as a second step in a process permitting folding and compression of the outer frame 102, according to the invention.

FIG. 36 is an illustration of a TOP view of a valve partially expelled from a delivery catheter 138, with a distal tab 268 leading the valve (along guide wire not shown) to the deployment location, with distal flow control component 130 beginning to open and showing two of three leaflets 258 opening from a folded, lie-flat configuration with the third leaflet opening from a folded configuration where it is folded back on itself when in the delivery catheter 138.

FIG. 37 is an illustration of a TOP view of a valve compressed 136 (side loaded) within a delivery catheter 138 with an outer frame 102 having a first tab 268 extending forward along a x-axis and a second trailing tab 270 extending backwards along the x-axis.

FIG. 38 is an illustration of an embodiment having multiple extendable anterior leaflet and/or chordae anchoring clips 111.

FIG. 39 is an illustration showing a process of using a distal tab to capture native tissue, according to the invention. FIG. 39 shows P2 capture via orthogonal delivery, followed by A2 capture. Steps include (1) providing a foldable, compressible orthogonal prosthetic mitral valve, (2) loading the valve sideways into a delivery catheter, (3) and advancing the valve to the heart via the IVC or SVC over a pre-placed guidewire that is threaded onto a subannuluar distal tab. The process then continues with (4) partially expelling the guide-wire tracking/straightened distal tab portion of the valve, (5) capturing the P2 leaflet and/or chordae by partially withdrawing guide wire to contract distal tab into its pre-curved configuration, (6) partially expelling the valve body to allow the leaflets to begin functioning and check for PVLs, (7) positioning valve body in annulus and completing deployment of the valve into the native annulus, and (8) actuating the A2 clip to capture anterior leaflet tissue.

ADDITIONAL DEFINITIONS AND PARTS LIST

Below is provide a parts list in relation to claimed elements. Part numbering may refer to functional components and may be re-used across differing preferred embodiments to aid in uniformly understanding structure-function relationships. To avoid cluttering in drawing sheets, not every number may be added to the drawing sheets.
100 A side delivered transcatheter prosthetic heart valve.
102 a self-expanding annular (outer) support frame.
103 Collar structure.
104 Central channel.
106 Outer perimeter wall.
107 Top edge of outer support frame.
108 Central vertical axis.
109 Z-axis, front to back, fold line axis.
110 Front wall portion of perimeter wall.
111 A2 clip
112 Back wall portion of perimeter wall.
113 A2 clip sleeve/pocket/sheath
114 Proximal side.
115 A2 clip steerable catheter/guidewire
116 Proximal fold area.
117 Secondary proximal fold areas.
118 Distal side.
119 A2 clip valve body attachment points
120 Distal fold area.
121 secondary distal fold areas.
122 Front upper collar portion.
123 A2 clip extendable hook portion, wire-W
223 post hook
323 loop hook
423 paddle hook
523 double loop hook
623 footer hook
723 fish trap hook
823 bent loop hook
124 Front lower body portion of outer frame.
125 A2 clip proximal portion
126 Back upper collar portion.
127 A2 clip locking (slidable) nut
128 Back lower body portion.
129 Sewn attachment points for inner to outer.
130 Flow control component, made of an inner frame having tissue leaflets mounted therein, collapsible (foldable and compressible), the inner mounted within the annular outer support frame and configured to permit blood flow in a first direction through an inflow end and block blood flow in the opposite, second direction, through the outflow end.
132 Inflow end.
134 Outflow end.
136 a compressed configuration
138 Delivery catheter.
140 X-axis, a horizontal axis, parallel to delivery. catheter central axis
142 Intersecting angle 45-135 degrees, X-axis to Y-axis.
143 Inner frame cover, top cover, mesh.
144 Expanded configuration.
146 Length-wise cylindrical axis of delivery catheter.
148 Height of about 5-60 mm.
150 Diameter of about 25-80 mm.
202 Plurality of compressible wire cells—outer frame.
204 Orientation and cell geometry substantially orthogonal to the central vertical axis to minimize wire cell strain when the annular support frame is compressed.
206 Vertical compressed configuration.
208 Folded configuration.
210 Folded and compressed configuration.
211 second A2 clip
212 Inner frame or outer frame shape selected from a funnel, cylinder, flat cone, or circular hyperboloid.
220 Braided matrix.
222 Wire frame matrix.
224 Laser-cut wire frame.
226 Biocompatible material.
227 Flared cuff on INNER frame.
228 Side profile of inner frame as a flat cone shape.
229 Non-cylindrical inner frame, e.g. elliptical section.
230 Diameter R of 40-80 mm.
231 INNER frame, for mounting leaflets.
232 Diameter r of 20-60 mm.
233 Set of uniform wire frame cells of INNER.
234 Height of 5-60 mm.
235 Non-uniform variable height cells of INNER.
236 Interior surface of annular outer support frame.
237 Non-uniform cell geometries, sizes in wire frame.
238 Exterior surface of annular outer support frame.
239. Compressed INNER.
240 Pericardial tissue for covering valve surfaces.
241 Diamond or eye-shaped wire cells.
242 Woven synthetic polyester material.
243 Eyelets on inner wire frame, consistent commissure attachment.
244 Outer support frame with an hourglass shape.
245 Laser cut attachment feature on inner frame.
246 Top diameter R1 of 40-80 mm.

248 Bottom diameter R2 of 50-70 mm.
250 Internal diameter r of 20-60 mm.
252 Height of 5-60 mm.
254 Internal diameter of 20-60 mm.
256 Height of 10-40 mm.
257 Leaflet band, mounting band for leaflet pockets.
258 LEAFLETS, plurality of leaflets, pericardial material.
259 Sewn edge of leaflet.
260 Rounded cylinder at an inflow end.
261 Open edge of leaflet
262 Flat closable aperture at an outflow end.
264 Longitudinal supports in/on flow control component, selected from rigid or semi-rigid posts, rigid or semi-rigid ribs, rigid or semi-rigid battons, rigid or semi-rigid panels, and combinations.
266 (any) Tab or tension arm extending from a distal side of the annular support frame.
268 DISTAL SUB-ANNULAR ANCHORING TAB, can be LVOT or other, comprised of wire loop or wire frame, integrated frame section, or stent, extending from about 10-40 mm away from the annular support frame.
269 Independent Distal tab.
270 PROXIMAL anchoring tab
271 D-shape
272 Distal upper edge of the annular support frame.
273 Upper atrial tension arm, comprised of wire loop or wire frame extending from about 2-20 mm away from the annular support frame.
274 Lower tension arm comprised of wire loop or wire frame, integrated frame section, or stent, extending from about 10-40 mm away from the annular support frame.
276 Distal side of the annular support frame.
278 Tissue anchors connected to the annular support frame for engaging native tissue.
280 Front wall portion of frame is a first flat panel.
282 Back wall portion of frame is a second flat panel.
284 Sewn seam.
285 Hinge.
286 Flexible fabric span without any wire cells.
287 Fabric panel.
288 Braided-wire cells.
289 Commissure attachment—leaflet to frame.
290 Laser-cut wire cells.
302 Rolling into a compressed configuration.
304 Bilaterally rolling into a compressed configuration.
306 Flattening the annular support frame into two parallel panels that are substantially parallel to the long-axis.
308 Compressing the annular support frame along a vertical axis to reduce a vertical dimension of the valve from top to bottom.
310 Rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.
311 Guide wire.
312 Steerable catheter for rotating the heart valve prosthesis along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.
314 A2 Clip for attachment to mitral A2 leaflet
316 A2 Clip Deployment Tool
434 Guide wire Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims.

Having thus described the invention with the details and particularity required by the patent laws, what is claimed and desired protected by Letters Patent is set forth in the appended claims:

1. A side-delivered prosthetic heart valve having an anterior leaflet anchoring tab component, comprising:
(i) a self-expanding annular outer support frame, said annular support frame having a central channel and an outer perimeter wall circumscribing a vertical y-axis in an expanded configuration, said outer perimeter wall having an anterior side, a posterior side, a distal side and a proximal side,
(ii) an integrated subannular anterior leaflet anchoring system mounted on the anterior side of the outer perimeter wall, wherein the system comprises
an anterior clip sleeve having a pre-loaded anterior clip disposed within a lumen of the sleeve,
the pre-loaded anterior clip comprising an elongated loop or tab, wherein said anterior clip is compressed or folded within the sleeve and a distal portion of the anterior clip presses against the outer perimeter wall when said anterior clip is compressed or folded, and
wherein said anterior clip is extended or unfolded when released from the sleeve along the cylindrical axis for capture of native leaflet or chordae tissue,
wherein the anterior clip engages with a guide wire during deployment to an extended or unfolded position allowing the anterior clip to capture native leaflet and/or native chordae, and upon withdrawal of the guide wire, the native leaflet and/or native chordae are sandwiched between the anterior clip and the outer perimeter wall of the annular support frame;
(iii) a collapsible flow control component mounted within the annular support frame,
the annular outer support frame and the collapsible flow control component comprising diamond- or eye-shaped wire cells made from heat-set Nitinol and configured to be foldable along a z-axis from a rounded or cylindrical configuration to a flattened cylinder configuration having a width of 8-12 mm, and compressible along a vertical y-axis to a shortened configuration having a height of 8-12 mm,
the collapsible flow control component having a leaflet frame with 2-4 flexible leaflets mounted thereon, wherein the 2-4 leaflets are configured to permit blood flow in a first direction through an inflow end of the collapsible flow control component and block blood flow in a second direction, opposite the first direction, through an outflow end of the collapsible flow control component;

(iv) a distal anchoring tab mounted on a distal side of the annular outer support frame, wherein the distal anchoring tab is an elongated member attached at a first end to the outer perimeter wall of the annular support frame and has an unattached second end that is heat set to a folded position to press against the outer perimeter wall, wherein the distal anchoring tab engages with a guide wire during deployment to an opened configuration, wherein the distal anchoring tab in the opened configuration tracks over the guide wire allowing the distal anchoring tab to capture native leaflet and/or native chordae, and upon withdrawal of the guide wire releasing the distal anchoring tab to the folded position, the native leaflet and/or native chordae are sandwiched between the folded distal anchoring tab and the outer perimeter wall of the annular outer support frame;

wherein the valve is compressible to a compressed configuration for introduction into the body using a delivery catheter for implanting at a desired location in the body, said compressed configuration is oriented along a horizontal x-axis at an intersecting angle of between 45-135 degrees to the vertical y-axis, and expandable to an expanded configuration having the horizontal x-axis at an intersecting angle of between 45-135 degrees to the vertical y-axis, wherein the horizontal x-axis of the compressed configuration of the valve is substantially parallel to a lengthwise cylindrical axis of the delivery catheter, wherein the valve has a height of about 5-60 mm and a diameter of about 25-80 mm.

2. The valve of claim 1, wherein the anterior clip has a radio-opaque marker.

3. The valve of claim 1, wherein the anterior clip comprises braided polyethylene, treated pericardial tissue, ePTFE, or Nitinol.

4. The valve of claim 1, wherein the annular outer support frame is comprised of a plurality of compressible wire cells having a orientation and cell geometry substantially orthogonal to the vertical y-axis to minimize wire cell strain when the annular outer support frame is configured in a vertical compressed configuration, a rolled compressed configuration, or a folded compressed configuration.

5. The valve of claim 1, wherein the annular outer support frame has a lower body portion and an upper collar portion, wherein the lower body portion in an expanded configuration forms a shape selected from a funnel, cylinder, flat cone, or circular hyperboloid, and wherein said annular outer support frame is comprised of a braided, wire, or laser-cut wire frame, and said annular outer support frame is covered with a biocompatible material, and wherein wherein the annular outer support frame has a diameter R of 40-80 mm, a diameter r of 20-60 mm, and a height of 5-60 mm.

6. The valve of claim 1, wherein the annular outer support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

7. The valve of claim 1, wherein the valve in an expanded configuration has a vertical y-axis that is substantially parallel to the first direction.

8. The valve of claim 1, wherein the flow control component has an internal diameter of 20-60 mm and a height of 10-40 mm, and a plurality of leaflets of pericardial material joined to form a rounded cylinder at an inflow end and having a flat closable aperture at an outflow end.

9. The valve of claim 1, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

10. The valve of claim 1, wherein the distal anchoring tab is comprised of wire loop, a wire frame, a laser cut frame, an integrated frame section, or a stent, and the distal anchoring tab extends from about 10-40 mm away from the distal side of the annular outer support frame.

11. The valve of claim 1, further comprising an upper distal anchoring tab attached to a distal upper edge of the annular outer support frame, the upper distal anchoring tab comprised of wire loop, a wire frame, a laser cut frame, an integrated frame section, or a stent, and extends from about 2-20 mm away from the annular outer support frame.

12. The valve of claim 1, comprising at least one tissue anchor connected to the annular outer support frame for engaging native tissue.

13. The valve of claim 1, wherein the outer perimeter wall comprises a front wall portion that is a first flat panel and a back wall portion that is a second flat panel, and wherein a proximal fold area and a distal fold area each comprise a sewn seam, a fabric panel, a rigid hinge, or a flexible fabric span without any wire cells.

14. The valve of claim 1, wherein the annular outer support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

15. A method for orthogonal delivery of implantable prosthetic heart valve to a patient, the method comprising the steps:

advancing a guide wire to an atrium, through the annular plane at an antero-posterior commissure, to a position behind a native posterior leaflet of a native heart valve of the patient;

advancing the prosthetic heart valve of claim 1 in a delivery catheter to the atrium of the patient, said prosthetic heart valve in a compressed configuration for side delivery, wherein the distal anchoring tab is threaded onto the guide wire, and wherein the anterior clip is optionally threaded onto the guide wire;

releasing the prosthetic heart valve of claim 1 from the delivery catheter, wherein the distal anchoring tab is in an open configuration and tracks over the guide wire during release;

advancing the prosthetic heart valve over the guide wire to move the distal anchoring tab to the position behind a native posterior leaflet and to seat the prosthetic heart valve into the native annulus;

withdrawing the guide wire to a first distal tab release position to release the distal anchoring tab to the folded position allowing the distal anchoring tab to capture native leaflet and/or native chordae, and sandwich the native leaflet and/or chordae between the folded distal anchoring tab and the outer perimeter wall of the annular outer support frame; and optionally withdrawing the guide wire to a second anterior clip release position to release the anterior clip to an open position allowing the anterior clip to capture native leaflet and/or native chordae, and sandwich the native leaflet and/or chordae between the anterior clip and the outer perimeter wall of the annular outer support frame.

16. The method of claim 15, wherein releasing the prosthetic heart valve from the delivery catheter is selected from the steps consisting of: (i) pulling the prosthetic heart valve out of delivery catheter using a rigid elongated pushing rod/draw wire that is releasably connected to a distal side of the prosthetic heart valve, wherein advancing the pushing rod away from the delivery catheter pulls the compressed prosthetic heart valve out of the delivery catheter, or (ii) pushing the prosthetic heart valve out of the delivery catheter using a rigid elongated pushing rod that is releasably connected to a proximal side of the prosthetic heart valve, wherein advancing the pushing rod out of from the delivery catheter pushes the compressed prosthetic heart valve out of the delivery catheter.

17. The method of claim 15, comprising the additional step of anchoring one or more tissue anchors attached to the prosthetic heart valve into native tissue.

18. The method of claim 15, comprising the additional step of rotating the prosthetic heart valve using a steerable catheter along an axis parallel to a plane of the native valve annulus.

* * * * *